US012755881B2

(12) United States Patent
Andrzejewski

(10) Patent No.: US 12,755,881 B2
(45) Date of Patent: Oct. 6, 2026

(54) MAGNETIC FIELD NULLING

(71) Applicant: SHIMADZU CORPORATION, Kyoto (JP)

(72) Inventor: Roch Andrzejewski, Manchester (GB)

(73) Assignee: SHIMADZU CORPORATION, Kyoto (JP)

( * ) Notice: Subject to any disclaimer, the term of this patent is extended or adjusted under 35 U.S.C. 154(b) by 222 days.

(21) Appl. No.: 18/707,527

(22) PCT Filed: Nov. 4, 2022

(86) PCT No.: PCT/EP2022/080827
§ 371 (c)(1),
(2) Date: May 3, 2024

(87) PCT Pub. No.: WO2023/079081
PCT Pub. Date: May 11, 2023

(65) Prior Publication Data

US 2024/0428974 A1 Dec. 26, 2024

(30) Foreign Application Priority Data

Nov. 5, 2021 (WO) ................ PCT/EP2021/080826

(51) Int. Cl.
*H01F 7/06* (2006.01)
*A61B 5/245* (2021.01)
(Continued)

(52) U.S. Cl.
CPC ............ *H01F 7/064* (2013.01); *A61B 5/245* (2021.01); *H01F 7/20* (2013.01); *H01F 13/00* (2013.01); *A61B 2562/18* (2013.01)

(58) Field of Classification Search
CPC .............. H01F 7/06; H01F 7/20; H01F 13/00; H01F 7/0164; A61B 5/245; A61B 2562/18; G01R 33/0094; G01R 33/025
(Continued)

(56) References Cited

U.S. PATENT DOCUMENTS

2012/0065491 A1* 3/2012 Borgert ................ A61B 5/0042 600/409
2013/0197838 A1 8/2013 Simola et al.
(Continued)

FOREIGN PATENT DOCUMENTS

JP 2000-037362 A 2/2000

OTHER PUBLICATIONS

Boto, Elena, et al. "Moving magnetoencephalography towards real-world applications with a wearable system." Nature 555.7698 (2018): 657-661.
(Continued)

*Primary Examiner* — Danny Nguyen
(74) *Attorney, Agent, or Firm* — Muir Patent Law, PLLC

(57) ABSTRACT

An apparatus for nulling a magnetic field within a nulling region in an external ambient magnetic field comprising a plurality of separate magnetic field generating elements 102 are located at separate respective locations surrounding the nulling region for generating respective nulling magnetic fields extending into the nulling region. A plurality of magnetic field sensing elements 103 are positioned at a plurality of respective separate locations within the nulling region for sensing respective values of the magnetic field within the nulling region. A feedback control unit 150 controls the values of the respective nulling magnetic fields generated by each of the plurality of magnetic field generating elements in response to values of the magnetic field sensed by the plurality of magnetic field sensing elements by
(Continued)

driving the magnetic field generating elements with respective electric currents that reduce the magnetic field values detected by respective magnetic field sensing elements to values not exceeding a pre-set threshold value corresponding to a pre-set nulling of the magnetic field within the nulling region.

40 Claims, 25 Drawing Sheets

(51) Int. Cl.
*H01F 7/20* (2006.01)
*H01F 13/00* (2006.01)

(58) Field of Classification Search
USPC .................................................. 361/139, 144
See application file for complete search history.

(56) References Cited

U.S. PATENT DOCUMENTS

2015/0219732 A1 8/2015 Diamond et al.
2017/0067972 A1* 3/2017 Diamond ........... G01R 33/1276

OTHER PUBLICATIONS

Holmes, Niall, et al. "A bi-planar coil system for nulling background magnetic fields in scalp mounted magnetoencephalography." NeuroImage 181 (2018): 760-774.
Littin, Sebastian, et al. "Development and implementation of an 84-channel matrix gradient coil." Magnetic resonance in medicine 79.2 (2018): 1181-1191.
Zhang, Rui, et al. "Recording brain activities in unshielded Earth's field with optically pumped atomic magnetometers." Science Advances 6.24 (2020): eaba8792.

* cited by examiner

Cross section

MAGNETIC FIELD NULLING

This application claims priority from PCT/EP2021/080826 filed 5 Nov. 2021, the contents and elements of which are herein incorporated by reference for all purposes.

FIELD OF THE INVENTION

The present invention relates to methods and apparatus for magnetic field nulling and particularly, although not exclusively, to methods and apparatus for magnetic field nulling in applications of Magnetoencephalography (MEG).

BACKGROUND

Magnetoencephalography (MEG) is a well-established medical technique for mapping brain electrical activity by recording magnetic fields that this activity generates. The magnetic fields generated by a brain are very weak and an environment in which there is effectively no (or negligible) ambient magnetic field environment is necessary to make them detectable. The magnetic field detecting sensors used in MEG are often based on superconducting quantum interference devices (SQUID). These devices require liquid helium cooling what is very costly. An alternative sensor technology is optically pumped magnetometers (OPM) that do not need cooling thereby reducing cost of the MEG apparatus.

An environment in which there is effectively no (or negligible) ambient magnetic field (e.g., for MEG applications) is usually delivered using large and very costly magnetically shielded rooms (MSR). These rooms typically comprise walls, floors and ceilings formed from a magnetically shielding material. Additionally, MSRs may be equipped with additional systems to cancel any remaining magnetic fields present within the MRS which may arise from limitations of the MSR or from equipment within it. The cost of MSRs is so significant that few institutions can effort MEG devices.

For MEG measurements, the patient must come to an MSR because the MEG device cannot be moved together with MSR to the patient. Inside the MSR, preferably only non-magnetic objects should be used to reduce additional ambient magnetic fields within the MSR. In addition, and MSR has very limited space and no windows. That limits possibility of bringing tools that can be used to interact with the patient, which is important for checking brain response. The static nature of the MSR prevents one from investigating patients in different environments, for example outside a building or in different environment bringing with it psychical comfort. This is particularly significant if an MSR environment is not comfortable for patients with claustrophobia or is scary for children.

Long-time patient monitoring, for example during sleep is very difficult within an MSR. In addition, an MSR prevents one from combining MEG measurements with other concurrent measurements requiring large devices for other techniques. For example, if one can remove the need for an MSR, this permits a concurrent measurement of MEG and low field MRI.

In addition, within an MSR one cannot avoid certain time varying magnetic field sources such as a patient's beating heart or power lines supplying power to MEG equipment within the MSR (e.g., a computer or the like). Where MSR itself needs additional compensation of such remaining internal magnetic fields, that may be delivered using Helmholtz coils or bi-planar coils placed inside the MSR.

The present invention has been devised in light of the above considerations.

SUMMARY OF THE INVENTION

The inventors have realised that concepts known from the field of super-diamagnetism, which occurs in some superconductors and result in exclusion of an external magnetic field from an internal region, the internal magnetic field. A superconductor is known to act as a virtually perfect diamagnetic material when placed in an external magnetic field. It excludes the field such that flux lines of the external magnetic field avoid the region of space occupied by the superconductor. This occurs because the external magnetic field generates electric currents on the surface of the superconductor which, in turn, generate an opposite magnetic field. The external magnetic field and surface-generated magnetic field cancel each other.

The inventors have realised that a knowledge of the external magnetic field on the surface is sufficient to allow one to cancel, or suppress to very small or negligible values, a magnetic field in a volume enclosed by that surface. This is supported by Stokes' theorem. Referring to FIG. 1, an external magnetic field 1*a* passes around, but not through, a diamagnetic material 1*b*. The reason for this effect lies in Stokes' theorem which relates the integral of the curl of a vector field over some surface, to the line integral of the vector field around the boundary of the surface. In other words, the line integral of a vector field over a loop is equal to the flux of its curl through the surface enclosed by that loop. FIG. 1 schematically shows a loop C enclosing a perfectly conducting 2-dimensional surface 1*c*. The surface can be imagined as comprising an array of contiguous surface elements or facets ($\Delta S_i$) each defining its own local enclosing loop (a square loop in this example). Imagine if this surface 1*c* is stretched over a spherical surface to form a 'bubble' (e.g., in the manner of blowing a bubble with bubble gum) with an opening defined by the boundary loop C, then imagine the size of the opening C being shrunk down to zero diameter. The result is a spherical surface within which no magnetic field exists, according to Stokes' theorem. The inventors have been motivated by applying this idea to a notional reference surface comprising an array of neighbouring separate magnetic field generating elements (e.g., conductive loops) each corresponding to a separate one of the surface elements or facets ($\Delta S_i$) of the notional reference surface (e.g., the spherical bubble described above) surrounding or enveloping a region of space within which an ambient magnetic field is to be nulled. The notional reference surface may fully enclose the region of space and may be notionally divided into a plurality of contiguous surface facets covering the whole of, or at least the majority of, the notional surface, and each one or the separate magnetic field generating elements may be arranged to reside in/on a respective one of plurality of contiguous surface facets. This may provide a structure approximating some or all of, the 'bubble' structure formed from surface 1*c* of FIG. 1.

At its most general, the invention is the idea of achieving cancellation (or 'nulling') of a magnetic field within a volume in similar manner to the principles underlying super-diamagnetics. By providing an array of magnetic field generating elements surrounding a volume of space and by applying a feedback control between those sensors and an array of magnetic field sensing elements inside that volume of space, one may control electric currents supplied to the magnetic field generating elements as necessary to effectively achieving cancellation (or 'nulling') of a magnetic field within the volume. In other words, the inventors have found that an indirect knowledge of the magnetic field at the surface of the volume of space over which the array of magnetic field generating elements are located, can be effectively obtained by achieving cancellation (or 'nulling') of a magnetic field within that volume of space. Once nulling is achieved, this means that the magnetic field at the surface of the volume of space is opposed in substantially equal measure over that surface by the array of magnetic field generating elements residing upon that surface.

The invention may, for example, may remove the need of MSR in a MEG system and may provide a cheaper and more compact solution. The invention may be applied to the nulling/cancelling of magnetic fields with time varying field gradients. The invention may simultaneously null/cancel both geomagnetic fields and gradient fields that are the result of magnetic sources in the surroundings and time varying and/or spatially moving magnetic sources.

In a first aspect, the invention may provide an apparatus for nulling a magnetic field within a nulling region in an (e.g., external) ambient magnetic field comprising:

- a plurality of separate magnetic field generating elements placed at separate respective locations surrounding the nulling region for generating respective nulling magnetic fields extending into the nulling region;
- a plurality of magnetic field sensing elements placed at a plurality of respective separate locations within the nulling region for sensing respective values of the magnetic field within the nulling region;
- a feedback control unit for controlling the values of the respective nulling magnetic fields generated by each of the plurality of magnetic field generating elements in response to values of the magnetic field sensed by the plurality of magnetic field sensing elements by driving the magnetic field generating elements with respective electric currents that reduce the magnetic field values detected by respective magnetic field sensing elements to values not exceeding a pre-set threshold value corresponding to a pre-set nulling of the magnetic field within the nulling region.

The feedback control unit may be arranged to determine a set of a plurality of optimal respective electric currents with which to drive the corresponding plurality of magnetic field generating elements by applying an orthogonal projection algorithm. The feedback control unit may be configured to generate a set of basis vectors for use in controlling the values of the respective nulling magnetic fields generated by each of the plurality of magnetic field generating elements, by applying the optimal respective electric currents. The feedback control unit may be configured to use the set of basis vectors in calculating respective optimal electric currents with which to drive magnetic field generating elements of the apparatus. The set of basis vectors may be based on a plurality of measured values of a magnetic field generated within the nulling region individually by each of the plurality of magnetic field generating elements (e.g., in isolation and as measured by the plurality of magnetic field sensing elements) when driven by a pre-set calibration electric current. The orthogonal projection algorithm may be arranged to generate an orthogonal basis set based on the plurality of measured values of a magnetic field generated within the nulling region individually by each of the plurality of magnetic field generating elements when driven by a pre-set calibration electric current.

The inventors have discovered that an orthogonal projection methodology may be very efficient and accurate in calculating the appropriate drive electric currents for generating magnetic fields to produce an effective nulling/cancelling of magnetic fields. Surprisingly, this methodology may require only one single calculation of the values for the drive electric currents. Calculation of drive currents may take less than 250 μs, for example. This is to be contrasted with other methodologies requiring several (and sometimes many) repeated calculations in which drive current values are repeatedly calculated many times in a process of iterative optimisation which tries to find ever-improved values for the drive currents (i.e., iterative improvement of nulling). These iterative processes are found to be much slower than the orthogonal projection methodology.

In this way, an external magnetic field (e.g., a geomagnetic field) may be nulled or cancelled. An external gradient magnetic field may be nulled or cancelled, or an external time varying magnetic field may be nulled or cancelled. The invention provides a system that can generate substantially magnetic-field-free conditions (or conditions of suitably negligible field) in a large volume with respect to the system size. Feedback sensors may control magnetic field generating elements (e.g., by controlling currents in coils) in a such way that magnetic field in the nulling volume is reduced by many orders of magnitude. The invention may be applied for nulling regions comprising complex gradient magnetic fields. In this way, the invention may be applied to avoid the need to use a magnetically shielded room (MSR) during the application of Magnetoencephalography (MEG) and/or may provide additional active nulling. A greater relative volume of nulled space, relative to the volume surrounded by the array of magnetic field generating elements, can be achieved as compared to other methods employing MSR or Helmholtz coils. Magnetic fields in the nulled region can be reduced to very low magnetic field levels and with high remaining field uniformity. It has been found that even more improvement, regarding low magnetic field levels with high remaining field uniformity, may be obtained simply by increasing number of magnetic field generating elements within the array.

Desirably, the feedback control unit comprises input terminals (e.g., for receiving feedback signals) connected to respective output terminals (e.g., for outputting magnetic field measurement signals) of the magnetic field sensing elements, and comprises on or more signal output terminals (e.g., for outputting control signals, or electrical drive currents) connected to the input terminals of associated magnetic field generating elements. For example, the one or more output terminals of the feedback control unit may be connected directly to respective input terminals of associated magnetic field generating elements. For example, each input terminal of an associated magnetic field generating element may be directly connected to an associated (e.g., dedicated) output terminal of the feedback control unit e.g., with that magnetic field generating element being the sole magnetic field generating element connected to that particular output terminal of the feedback control unit. This connection between a given output terminal of the feedback control unit and the input terminal of an associated magnetic field generating element, may conduct a respective electric current for direct use by the associated magnetic field generating element in generating a magnetic field required to reduce the magnetic field values detected by respective magnetic field sensing elements. Alternatively, the one or more output terminals of the feedback control unit may be connected indirectly to respective input terminals of associated magnetic field generating elements, via an intermediate current supply unit (or units) configured to receive current supply control signals from the feedback control unit and to be responsive to receipt of such current supply control signals to supply a specified current to one or more (or each) respective specified magnetic field generating elements. The specified currents and specified magnetic field generating elements may be specified within the current supply control signals.

Desirably, the feedback control unit is configured to analyse each signal from each magnetic field sensing element to determine how to adjust or regulate electrical currents supplied to associated magnetic field generating element in the direction that reduces the value of the sensed magnetic field readings from the magnetic field sensing elements.

The feedback control unit is preferably configured to continuously monitor (e.g., in uninterrupted fashion for a given duration of time, or intermittently) the magnetic field values provided by the magnetic field sensing elements within the nulling volume and to continuously control the respective electrical currents supplied to the correcting magnetic field generating element. In this way, active field nulling can be provided.

Preferably, the plurality of magnetic field generating elements comprises at least 10 separate magnetic field generating elements, or more preferably at least 50 separate magnetic field generating elements, or yet more preferably at least 200 separate magnetic field generating elements. Preferably, the plurality of magnetic field generating elements comprises at least about 100 elements and not more than about 4000 elements or not more than about 3000 elements or not more than about 2000 elements.

Preferably, the magnetic field generating elements comprise electrically conductive coils adapted for conducting said electric currents. Each magnetic field generating element may comprise an electrically conductive coil. A coil of a magnetic field generating element may comprise a circular coil or other shaped coil, for example a polygonal coil (e.g., hexagonal). A coil of a magnetic field generating element may be substantially flat or planar such that all turns of the coil reside substantially in the same plane. The diameter of each coil (e.g., the diameter of the loop or winding of the coil) of the array of magnetic field generating elements may be substantially the same as the diameter of a plurality of other coils of the array of magnetic field generating elements, or may be the same as the diameter of every other coil of the array of magnetic field generating elements. For Dual Geodesic Icosahedron lattices, the coils that placed on hexagonal elements/facets of the lattice may be larger than coils that are placed on pentagonal elements/facets of the lattice. Preferably, the array of magnetic field generating elements may comprise a mixture of coils with different diameters. This is preferably the case when a geodesic lattice is used. This can help achieve better lattice coverage. Good lattice coverage may be achieved using coils of the same diameter as each other when the lattice defining the array of magnetic field generating coils is defined according to a Platonic solid.

Alternatively, a coil of a magnetic field generating element may be configured such that turns of the coil are arranged in a stacked arrangement (e.g., helically spiralling) such that all turns of the coil are substantially planar and plane-parallel, but successive turns of the coil are distributed longitudinally in a direction perpendicular to the plane of the turns. The extent of longitudinal distribution is preferably small relative to the extent of the lateral dimension of each coil. In other words, each coil is preferably 'thin' to save on space. The lateral dimension (e.g., diameter) of the turn(s) of the coil exceeds the longitudinal dimension of the coil perpendicular to the lateral dimension by a factor of at least 4 (e.g., four times wider than it is thick), or more preferably at least 5, or yet more preferably at least 7, or even more preferably at least 10.

A coil may comprise one winding or loop of a conductive wire, track or strip, or a plurality of windings or loops of a conductive wire, track or strip defining. A coil may comprise a current input terminal, a current output terminal and one or more windings or loops electrically connecting the two terminals such that current input via the input terminal travels around the winding(s) or loop(s) before reaching the current output terminal. The loops or windings of a coil may repeat a common loop or winding shape, such that loops or windings share substantially of the same shape, dimensions and orientation as each other. Alternatively, loops or windings of a coil may define a spiral shape of increasing or decreasing spiral radius (e.g., a flat spiral).

Preferably, each coil is configured to face in a direction towards the centre or centroid of the array of magnetic field generating elements. A direction in which a coil "faces" may be considered to be a direction perpendicular to the plane containing a diameter of the coil. A direction in which a coil "faces" may be considered to be a direction parallel to the winding axis of the coil (i.e., the axis about which the windings wind, such as the coil's symmetry axis). In this way, the direction in which a coil "faces" may define the orientation with which the magnetic field produced through the centre of that coil is parallel when driven by a current. The direction of that magnetic field may be controlled by controlling the direction a given current flow direction through the coil. The direction of a current through a coil may be defined, for example, in terms of whether the current flow is clockwise or anticlockwise when viewing the coil in a direction facing towards the centre of the array of magnetic field generating elements. For example, a given current flow within a given coil may be defined as "positive" when viewed from one side of the coil and "negative" either when viewed from the opposite side (i.e., a reversal of the direction of view) or when the coil is rotated by 180 degrees to present to the static viewer its opposite side (i.e., a reversal of the 'face' of the coil).

The coil orientations within the array of separate magnetic field generating elements most preferably differ, relative to other coils in the array, according to the position of the coil in question within the array. In other words, the position of a coil within the array also determines its orientation (i.e., the direction it "faces") relative to the centroid of the array. The direction of the electrical current with which separate coils are driven most preferably differ, relative to other coils in the array, according to the position of the coil in question within the array. In other words, the position of a coil within the array also determines the direction of the electrical current driven through the coil. The direction of the current within a coil may be defined relative to the local coordinate system of the coil in question. Each individual coil local coordinate system may be arranged in an orientation or position that is rotated relative to coil local coordinate system its neighbouring coils (or all coils) in the array of coils.

Preferably, each coil of the array of magnetic field generating elements is electrically separate (e.g., isolated) from any other coil of the array of magnetic field generating elements. This allows each coil to be driven independently of any of the other coils, permitting great flexibility in controlling the array of magnetic field generating elements to achieve nulling. Neighbouring coils in the array of magnetic field generating elements may at least partially overlap or may be arranged such that no coils of the array overlaps any other neighbouring coil of the array.

Optionally the coils of the array of magnetic field generating elements may comprise a plurality of sub-groups comprising three coils each one of which faces in a respective one of three mutually perpendicular directions. For example, the directions in which the coils of the sub-group face may correspond to a local orthogonal trial (i.e., the x-y-z coordinate directions centred upon the centre of the sub-group). Preferably, the direction in which any one coil of the subgroup of coils faces is a direction that is substantially perpendicular to the direction in which each of the other coils of the sub-group face such no two coils of the sub-group of coils face in the same direction. This arrangement of sub-groups of coils permits additional control over the vector direction of parts of the local magnetic field in and around the region occupied by the coils of the respective sub-group of coils. One coil of each sub-group of coils may be configured to face in a direction towards the centre or centroid of the array of magnetic field generating elements.

Desirably, the plurality of magnetic field generating elements are arranged at said separate respective locations in a first array shaped according to a three-dimensional reference surface surrounding the nulling region. Preferably, the plurality of magnetic field sensing elements are arranged at said separate respective locations defining a second array shaped according to a three-dimensional reference surface. It is to be understood that the reference surface may or may not be a physical surface. If the reference surface is a physical surface (i.e., it coincides with a physical surface) then it may provide the function of a support surface upon which magnetic field generating elements are arranged (e.g., attached) so as to constrain and retain the positions of the magnetic field generating elements to conform to the desired array pattern. The support surface may be a continuous surface or may be a scaffold to which the magnetic field generating elements are attached at locations of the scaffold coinciding with locations of a notional reference surface. For example, the support surface may be a spherical shell surface coinciding with a notional spherical reference surface. Alternatively, the support surface may comprise a 3-dimensional polyhedron scaffold the vertices of which coincide with points on the surface of a sphere. The magnetic field generating elements may be attached to this support surface at respective vertices or respective groups of vertices, or at scaffold edges (e.g., polygon edges forming notional facets of the polyhedron) extending between vertices.

The support surface (e.g., continuous surface or scaffold) may be mounted on a pivoted support assembly that permits rotation of the support surface about at least one spatial axis, or at least two orthogonal spatial axes or about all three orthogonal spatial axes. The pivoted support assembly may comprise an altitude-azimuth mounting ("Alt-Az" mount) permitting independent adjustment of the azimuth pointing position and the altitude pointing position of the support surface. In this way, the support surface (e.g., scaffold) may be oriented (and any array of magnetic field generating coils and magnetic field sensing elements upon it) in a direction against the direction of the geomagnetic field vector. This may assist in achieving better nulling.

Preferably, the second array (i.e., defined by the plurality of magnetic field sensing elements) is configured to be substantially concentric with the first array (i.e., of magnetic field generating elements). The inventors have found that this arrangement permits particularly accurate and effective nulling within an nulling region. The separate respective locations in the first array may be defined according to a regular lattice. The locations may coincide with (or be defined by) notional vertices or facets of a polyhedron. The separate respective locations in the second array may be defined according to a regular lattice. Preferably, the plurality of magnetic field generating elements are arranged at said separate respective locations substantially equidistant from the centre of the nulling region thereby defining a substantially spherical array surrounding the nulling region.

Preferably, the plurality of magnetic field sensing elements are arranged at said separate respective locations substantially equidistant from the centre of the nulling region thereby defining a substantially spherical array within the nulling region.

Desirably, the size of a diameter of the array of magnetic field sensing elements is at least about 40% of the size of a diameter of the array of magnetic field generating elements. The inventors have found that particularly effective field nulling may be achieved when this condition is applied. Desirably, the size of a diameter of the array of magnetic field sensing elements is between about 40% and about 90% of the size of a diameter of the array of magnetic field generating elements. More preferably, the size of a diameter of the array of magnetic field sensing elements is between about 40% and about 80% of the size of a diameter of the array of magnetic field generating elements. Preferably, the size of a diameter of the array of magnetic field sensing elements is between about 40% and about 90% of the size of a diameter of the array of magnetic field generating elements and the array of magnetic field generating elements comprises more at least about 200 elements and not more than about 2000 elements. The inventors have found that especially effective field nulling may be achieved when one or more of these conditions is applied.

Preferably, the threshold value is not greater than $5\times10^{-9}$ Tesla or is more preferably not greater than $5\times10^{-10}$ Tesla.

The magnetic field sensing elements may comprise one or more of: Hall effect sensors (e.g., for μT fields); magneto-impedance sensors (e.g., to cover the μT to nT range); fluxgate sensors (e.g., to cover the μT to nT range); Optically Pumped Magnetometer (OPM) sensors (e.g., to cover for nT-fT range). Such three sensors can be used as one sensor feedback group with extended sensing range.

The number of magnetic field sensing elements may be fewer in number than the number of magnetic field generating elements. The feedback control unit may be configured to generate magnetic field values associated with one or more locations within the nulling region by interpolating between a plurality magnetic field values sensed by a plurality of magnetic field sensing elements of the array of sensing elements. The control unit may be configured to define a notional interpolation sphere defined by a radius from a target position (coordinates) within the nulling region at which a magnetic field value is to be interpolated. The control unit may be configured to determine which of the magnetic field sensing elements are located within the notional sphere (and may increase the radius of the sphere until at least two sensors are within the sphere). The control unit may be configured to calculate an interpolated value of the magnetic field at the target position by three-dimensional interpolation of magnetic field values received by it from the plurality of sensors within the interpolation sphere.

The feedback control unit may be configured to generate a set of basis vectors for use in controlling the values of the respective nulling magnetic fields generated by each of the plurality of magnetic field generating elements. The feedback control unit may be configured to use the set of basis vectors in calculating respective electric currents with which to drive magnetic field generating elements of the apparatus. The feedback control unit may be configured to supply each magnetic field generating element in turn by an electric current alone while all other magnetic field generating elements receive no electric current therefrom. The feedback control unit may be configured to obtain from the magnetic field sensing elements measured values of the magnetic field within the apparatus sensed by each of the magnetic field sensing elements at their respective fixed locations within the nulling region. The feedback control unit may be configured to use these measured magnetic field values as calibration values to define a basis vector for the magnetic field generating element to which the current was supplied. The control unit may be configured to repeat this process separately for each magnetic field generating element of the array of coils whereby each magnetic field generating element separately takes the role of being the lone magnetic field generating element supplied with electric current. For each magnetic field generating element, of an array of m elements, the control unit may be configured to construct a respective basis vector based on calibration magnetic field values received from all n sensors. For example, the basis vector for a first coil may be:

$$[Bx_{11}, By_{11}, Bz_{11} \ \ldots \ Bx_{1n}, By_{1n}, Bz_{1n}]$$

The array of m coils the feedback control unit may be arranged to generate a matrix of basis vectors constructed using the respective basis vectors for all m magnetic field generating elements:

$$\begin{bmatrix} Bx_{11}, By_{11}, Bz_{11} & \cdots & Bx_{1n}, By_{1n}, Bz_{1n} \\ \vdots & \ddots & \vdots \\ Bx_{m1}, By_{m1}, Bz_{m1} & \cdots & Bx_{mn}, By_{mn}, Bz_{mn} \end{bmatrix}$$

The feedback control unit may be arranged to implement active cancelation of an ambient magnetic field by performing calculations of the value and direction of an electrical drive current, to supply to respective magnetic field sensing elements, based on these unit vectors. The feedback control unit may be arranged such that each measurement of a magnetic field from a magnetic field sensing element, with all sensing elements subsequently operating in an active cancelation function is defined as a pseudo-vector type matrix construct:

$$[Sx_1, Sy_1, Sz_1 \ \ldots \ Sx_n, Sy_n, Sz_n]$$

Making:

$$N = 3n, M = 3m$$

$$Bx_{11}, By_{11}, Bz_{11}, Bx_{12}, By_{12}, Bz_{12} \ldots = X_{11}, X_{12}, X_{13}, X_{14}, X_{15}, X_{16} \ldots$$

$$Sx_1, Sy_1, Sz_1, Sx_2, Sy_2, Sz_2 \ldots = V_1, V_2, V_3, V_4, V_5, V_6 \ldots$$

An equation for orthogonal projection is:

$$\sum_{j=1}^{M}\left(\sum_{k=1}^{N} X_{jk} \cdot X_{ik}\right)\alpha_j = \sum_{k=1}^{N} V_k X_{ik}$$

The terms $\alpha_j$ are terms containing the current for the jth magnetic field generating element. To achieve cancelation the control unit may be configured to calculate the 'negative' values of currents with which each magnetic field generating coil must be driven by solving the following optimisation equation:

$$\sum_{j=1}^{M}\left(\sum_{k=1}^{N} X_{jk} \cdot X_{ik}\right)\alpha_j = -\sum_{k=1}^{N} V_k X_{ik}$$

The feedback control unit may be configured to vary the value of the currents applied to each magnetic field generating element by varying the values of $\alpha_j$ in the above equation in order to reduce the value of the magnetic field measured by the magnetic field sensing elements collectively (e.g., as averaged amongst them) or individually to not exceed a desired pre-set threshold value corresponding to an appropriate level of field cancellation/nulling.

The feedback control unit may be arranged to calculate the values of currents, $\alpha_j$, with which each magnetic field generating element must be driven by solving the following optimisation equation in respect of the parameters $\alpha_j$:

$$\sum_{j=1}^{M}\left(\sum_{k=1}^{N} X_{jk} \cdot X_{ik}\right)\alpha_j = -\sum_{k=1}^{N} V_k X_{ik}$$

It is to be noted that the orthogonal projection algorithm may calculate "optimal" electric drive currents appropriate for field nulling/cancelation currents directly as a result of solving (e.g., inverting) the above equation in respect of the parameters $\alpha_j$. In this sense, it is to be understood that the word "optimisation" refers to calculating the values of the parameters $\alpha_j$, which are inherently deemed to be optimal by the nature of the above equation. This is not the same as prior art "optimisation" methodologies which often require many iterations in a much less efficient iterative methodology of magnetic field minimisation. Put in other words, for comparison, one may consider the orthogonal projection methodology discussed herein as requiring only one single calculation of the parameters $\alpha_j$, giving immediately what is needed, without requiring any subsequent "iteration" calculations to find "improved" values of those parameters.

The feedback control unit may be arranged to use readings, $V_k$, from the magnetic sensing elements. These readings may be placed in a matrix of readings by the control unit (e.g., $[V_1, V_2, V_3, \ldots, V_N]$). The measurements of a magnetic field may include measurements (Sx, Sy, Sz) of three orthogonal field components by each of the magnetic sensing elements. The feedback control unit may be arranged to calculate a dot product of the matrix of readings and the orthogonal basis vectors of the magnetic field generating elements, as:

$$\sum_{k=1}^{N} V_k X_{ik}$$

Here, the sensor readings and the matrix elements of the matrix of sensor readings are related as:

$$Sx_1, Sy_1, Sz_1, Sx_2, Sy_2, Sz_2 \ldots = V_1, V_2, V_3, V_4, V_5, V_6 \ldots$$

In this way, a plurality (e.g., three) sensor readings may be produced for each sensor position and these correspond to a plurality of orthogonal magnetic field directions (e.g., x, y, z). The orthogonal basis vector elements are related to the magnetic field components (e.g., in three orthogonal component directions: x, y, z) generated by the magnetic field generating elements as:

$$Bx_{11}, By_{11}, Bz_{11}, Bx_{12}, By_{12}, Bz_{12} \ldots = X_{11}, X_{12}, X_{13}, X_{14}, X_{15}, X_{16} \ldots$$

Thus, the elements $X_{ik}$ may correspond to magnetic field components (Bx, By, Bz) that would be generated by individual magnetic field generating elements in three orthogonal directions in response to being driven by drive current represented by currents, $\alpha_j$, The feedback control unit may be arranged to use the resulting dot product to invert the above optimisation equation. The control unit may be arranged to generate a matrix containing individual values, $\alpha_j$, for the currents with which to drive the magnetic field generating elements individually. This has been found to be a particularly time-efficient processing method.

In general, only a few iterations (typically, only one iteration) is necessary to get the best current solution for external magnetic field nulling/cancelling. The orthogonal basis for the orthogonal projection method is preferably created in the above calibration process. The orthogonal basis need only be created once and may subsequently be used by the control unit for all active cancellation/nulling using sensor data received from the magnetic field sensor array during active cancelling/nulling operations. The above calibration process (i.e., determination of calibration magnetic fields, creation of an orthogonal basis) may be performed (e.g., once) in an environment containing substantially no environmental or ambient magnetic field (i.e., within a magnetically shielded room (MSR)). This may be done during manufacture of the apparatus, or periodically through the lifetime of the apparatus (i.e., re-calibration) as and when appropriate. The apparatus, once calibrated, may be used outside a magnetically shielded room (MSR) thereafter.

Alternatively, the calibration can be performed in the standard environment (i.e., not within an MSR) containing geomagnetism and magnetic field gradients from the local environment (e.g., electrical components, electronics etc.). To perform calibration in such environments, the apparatus may be arranged as follows.

The feedback control unit may be configured to generate the set of basis vectors by obtaining correction values corresponding to measured values of the magnetic field within the apparatus sensed by each of the magnetic field sensing elements at their respective fixed locations within the nulling region either:

(a) when no drive electric current is supplied to any of the magnetic field generating elements (i.e., such that measured values correspond to environmental/geomagnetic values), or (b) when a pre-set drive electric current is supplied to each of the magnetic field generating elements; and subtracting the correction values from the calibration values generated by supplying (as noted above) each magnetic field generating element in turn by an electric current alone while all other magnetic field generating elements receive no electric current therefrom.

This provides corrected calibration values for use to define the basis vectors. In this way, the readings of the magnetic field sensing elements (feedback sensors) may be effectively set to zero (i.e., are zeroed against internal magnetic fields) during the calibration process.

The feedback control unit may be configured to cease subtracting the correction values from the measurement values generated by each magnetic field generating element after the calibration process has been completed (i.e., immediately after). This means that the actual readings of the magnetic field generating element are set back to true readings (i.e., without the aforementioned 'zeroing') and the process of orthogonal projection may ensue. The consequence of this is the that the basis vectors if the orthogonal projection inherently subtract the internal magnetic field present under (a) or (b) above. The experimental results illustrated in FIGS. 27*a*, 27*b* and 27*c* were generated as a result of calibration done this way without the use of an MSR.

The pre-set drive electric current (noted at point (b) above) may be the same for each of the magnetic field generating elements or may differ as between different respective magnetic field generating elements. The benefit of a pre-set drive electric current is so as to produce a magnetic field in the environment of the magnetic field sensing elements which is able to partially null the environmental/geomagnetic field to a sufficient extent to reduce the strength of that field to a value that falls within the dynamic range of the magnetic field sensing elements. Note that the typical strength of an environmental/geomagnetic field is much higher than the dynamic range of some magnetic field sensing elements which would saturate were it not for the use of the pre-set drive electric currents. This allows the process of generating basis vectors (calibration) and subsequent orthogonal projection to proceed using magnetic field generating elements of any desired dynamic range.

Accordingly, while it can be advantageous to calibrate the apparatus in an MSR, if this is available and convenient, the invention may provide means for performing calibration when no MRS is available. Indeed, this also means that calibration could be performed every time the apparatus is used. The advantage of this is that any mechanical change to the positioning of magnetic field generating elements and/or magnetic field sensing elements is removed. Also, changes in the temperature of the apparatus may affect the performance of magnetic field sensing elements, and these changes would be taken into account by the calibration process.

In a second aspect, the invention may provide a method for nulling a magnetic field within a nulling region in an (e.g., external) ambient magnetic field comprising:

providing a plurality of separate magnetic field generating elements placed at separate respective locations surrounding the nulling region for generating respective nulling magnetic fields extending into the nulling region;

providing a plurality of magnetic field sensing elements placed at a plurality of respective separate locations within the nulling region for sensing respective values of the magnetic field within the nulling region;

controlling the values of the respective nulling magnetic fields generated by each of the plurality of magnetic field generating elements in response to values of the magnetic field sensed by the plurality of magnetic field sensing elements by driving the magnetic field generating elements with respective electric currents that reduce the magnetic field values detected by respective magnetic field sensing elements to values not exceeding a pre-set threshold value corresponding to a pre-set nulling of the magnetic field within the nulling region.

Preferably, according to the method, the magnetic field generating elements comprise electrically conductive coils and the method includes conducting said electric currents thought respective said coils.

The method may include providing the plurality of magnetic field generating elements as arranged at said separate respective locations in a first array shaped according to a three-dimensional reference surface surrounding the nulling region.

The method may include providing the plurality of magnetic field sensing elements as arranged at said separate respective locations defining a second array shaped according to a three-dimensional reference surface.

The method may include providing the second array so as to be substantially concentric with the first array.

Desirably, in the method, the separate respective locations in the first array are defined according to a regular lattice. Desirably, the separate respective locations in the second array are defined according to a regular lattice, according to the method.

The method may include providing the plurality of magnetic field generating elements as arranged at said separate respective locations substantially equidistant from the centre of the nulling region thereby defining a substantially spherical array surrounding the nulling region.

The method may include providing the plurality of magnetic field sensing elements as arranged at said separate respective locations substantially equidistant from the centre of the nulling region thereby defining a substantially spherical array within the nulling region.

Desirably, in the method, the size of a diameter of the array of magnetic field sensing elements is at least 40% of the size of a diameter of the array of magnetic field generating elements.

The method may include providing the plurality of magnetic field generating elements to comprise at least separate magnetic field generating elements, or more preferably at least 50 separate magnetic field generating elements, or yet more preferably at least 200 separate magnetic field generating elements.

A method may include receiving inputs at the feedback control unit that correspond to the outputs from the magnetic field sensing elements and providing outputs from the feedback control unit comprising control signals that are input to associated magnetic field generating elements.

Preferably, the threshold value is not greater than $5\times10^{-9}$ Tesla, or more preferably is not greater than $5\times10^{-10}$ Tesla.

The method may comprise generating magnetic field values associated with one or more locations within the nulling region by interpolating between a plurality magnetic field values sensed by a plurality of magnetic field sensing elements of the array of sensing elements. The method may include defining a notional interpolation sphere defined by a radius from a target position (coordinates) within the nulling region at which a magnetic field value is to be interpolated. The method may include determining which of the magnetic field sensing elements are located within the notional sphere (and may increase the radius of the sphere until at least two sensors are within the sphere). The method may include calculating an interpolated value of the magnetic field at the target position by three-dimensional interpolation of magnetic field values sensed by the plurality of sensors within the interpolation sphere.

In another aspect, the invention may provide a magnetoencephalography apparatus comprising one or more Magnetoencephalography (MEG) sensors configured to be distributed about the head of a patient, and an apparatus according to the first aspect of the invention for nulling a magnetic field within a nulling region dimensioned to accommodate the head of the patient. The apparatus according to the first aspect of the invention may be configured to cancel the ambient magnetic field within the nulling region (e.g., Earth's magnetic field and magnetic fields generated by surrounding objects) containing the magnetic field sensing elements of the apparatus and patient head. In a further aspect, the invention may provide a medical imaging apparatus comprising the magnetoencephalography apparatus described above, and/or a brain activity mapping apparatus comprising the magnetoencephalography apparatus described above, and/or a biomagnetism sensing apparatus comprising the magnetoencephalography apparatus described above, and/or a neurofeedback apparatus comprising the magnetoencephalography apparatus described above, and/or a brain-computer interface apparatus comprising the magnetoencephalography apparatus described above.

When used in MEG applications, for example, field nulling with the proposed invention can be provided inside an MSR. This method can be used to cancel any remaining magnetic fields within an MSR (e.g., from equipment). When used in MEG applications or another medical application, the array of magnetic field generating elements may be dimensioned and configured to surround a region (e.g. volume) of space sufficient to accommodate the whole subject body of a patient or a body part other than a patient's head. The array of magnetic field sensing elements may be similarly dimensioned and configured.

The invention, in any aspect, may provide shielding for magnetocardiography (MCG), or for magnetomyography (MMG), or for magnetoneurography (MNG). The invention, in any aspect, may provide shielding for nerve signal propagation in the lumbar spine for magnetospinography (MSG). The invention, in any aspect, may provide shielding for the cervical spinal cord evoked field (SCEF) measurements. The invention, in any aspect, may provide shielding for the brain computer interface (BCI) based on MEG.

In some of these applications, shielding with the proposed invention can be deliver over whole human or animal body or different body parts.

In yet another aspect, the invention may provide a method of Magnetoencephalography comprising distributing one or more Magnetoencephalography (MEG) sensors about the head of a patient and nulling a magnetic field within a nulling region dimensioned to accommodate the head of the patient according to the invention in its second aspect.

The invention includes the combination of the aspects and preferred features described except where such a combination is clearly impermissible or expressly avoided.

SUMMARY OF THE FIGURES

Embodiments and experiments illustrating the principles of the invention will now be discussed with reference to the accompanying figures in which.

DETAILED DESCRIPTION OF THE INVENTION

Aspects and embodiments of the present invention will now be discussed with reference to the accompanying figures. Further aspects and embodiments will be apparent to those skilled in the art. All documents mentioned in this text are incorporated herein by reference.

Figures 2A, 2B:
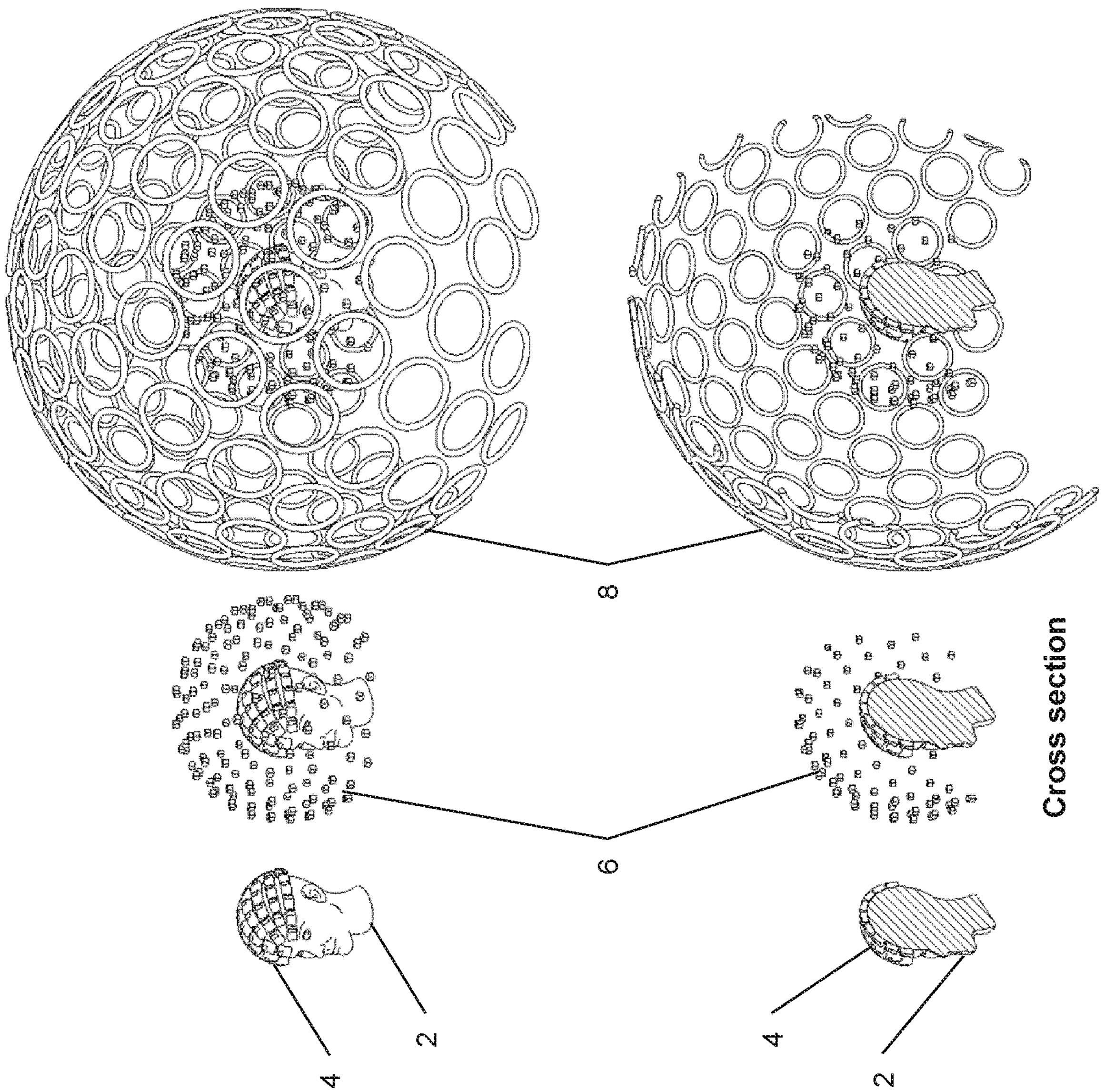
FIG. 2*a* and FIG. 2*b* show elements of a magnetic field nulling apparatus and a cross-sectional view of thereof, respectively.

FIG. 2*a* shows an apparatus for nulling a magnetic field within a nulling region in an external ambient magnetic field. FIG. 2*b* shows the apparatus in cross-section. The apparatus comprises a plurality of separate magnetic field generating coil elements 8 each comprising a circular loop of mutually common diameter and each being placed at separate respective location upon a first notional spherical shell reference surface surrounding the nulling region for generating respective nulling magnetic fields extending into the nulling region. Each one of the magnetic field generating coil elements 8 comprises an electrical current input terminal (not shown) and a current output terminal (not shown) for the inputting and outputting, respectively, of a drive current to the coil in question.

A plurality of magnetic field sensing elements 6, for example OPM sensors, are placed at a plurality of respective separate locations within the nulling region for sensing respective values of the magnetic field within the nulling region. The magnetic field sensing elements are also placed at separate respective locations upon a second notional spherical shell reference surface surrounding the nulling region. The first and second spherical shell reference surfaces are concentric, with the diameter of the first reference spherical shell surface being about 2.5 times the diameter of the second reference spherical shell surface.

A patient's head 2 is placed within the nulling region within the spherical shell array of the plurality of magnetic field sensing elements 6 so as to coincide with the centres of the first and second reference spherical shells.

A feedback control unit (not shown, see item 150 FIG. 19) is arranged to control the values of the respective nulling magnetic fields generated by each of the plurality of magnetic field generating elements 8 in response to values of the magnetic field sensed by the plurality of magnetic field sensing elements 6 by driving the magnetic field generating elements with respective electric currents that reduce the magnetic field values detected by respective magnetic field sensing elements to values not exceeding a pre-set threshold value corresponding to a pre-set nulling of the magnetic field within the nulling region.

Each magnetic field generating coil 8 is configured to face in a direction towards the centre or centroid of the array of magnetic field generating elements. In other words, each coil "faces" in a direction perpendicular to the plane containing a diameter of the coil. The direction in which each coil "faces" is a direction parallel to the winding axis of the coil (i.e., the axis about which the windings wind, such as the coil's symmetry axis). In this way, the direction in which a coil "faces" defines the orientation with which the magnetic field produced through the centre of that coil is parallel when driven by a current. The direction of that magnetic field is controlled by controlling the direction a given current flow direction through the coil.

Each coil 8 of the array of magnetic field generating elements is electrically separate and electrically isolated from any other coil of the array of magnetic field generating elements and each coil is driven independently of any of the other coils. Neighbouring coils in the array of magnetic field generating elements are arranged such that no coils of the array overlaps with any other neighbouring coil of the array. In other examples, neighbouring may at least partially overlap.

The patient 2 is shown wearing a MEG sensor cap 4, in this case OPM sensors are covering the patient's head. The magnetic field sensors 6 are distributed around MEG sensor cap 4 at a safe distance. The patient's brain magnetic field cannot be seen by magnetic field sensors 6. The magnetic field sensors 6 and the coils 8 each form a spherical lattice with an opening at its base for admitting the patient's head 2. It is to be noted that the invention is flexible in the sense that it does not need to use a lattice array coverage of magnetic field generating elements that cover the while of the spherical shell reference surface shape, and different notional reference surface shapes can be used. For example, the notional reference surface may be a spheroid or cylindrical shape. Because cancelling/nulling is achieved by electronic control of currents in the magnetic field generating elements 8, a variety of positioning of the magnetic field generating elements problem can be used. This gives flexibility in shaping array of the magnetic field generating elements.

Figure 3A:
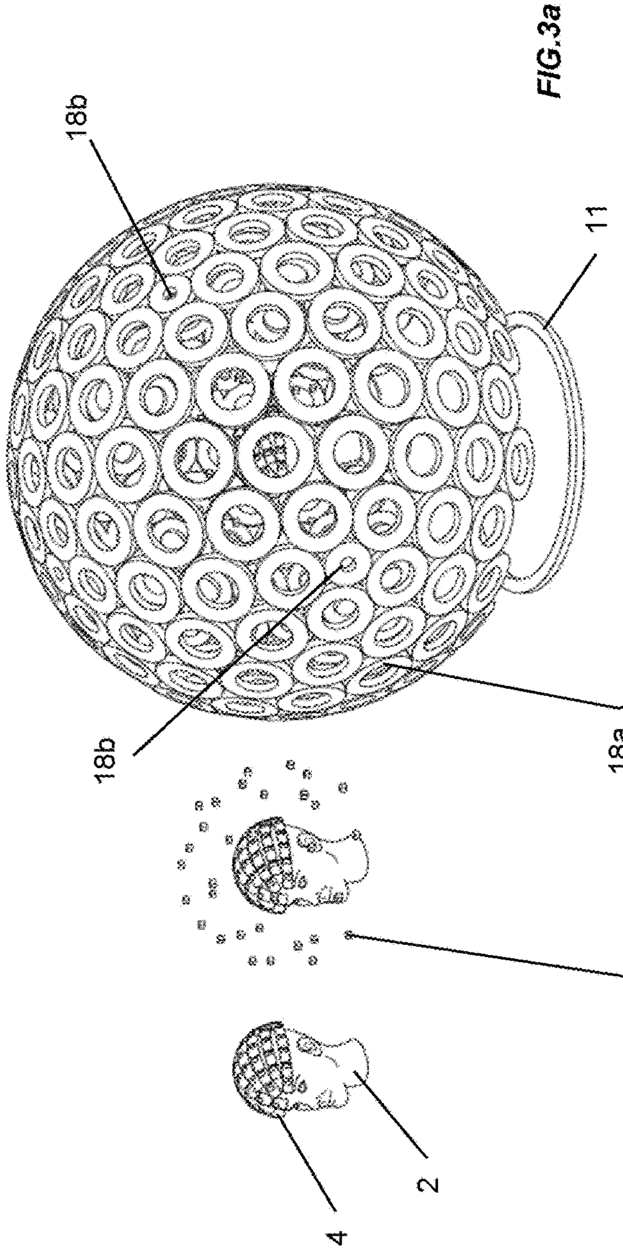
FIG. 3*a* and FIG. 3*b* show elements of a magnetic field nulling apparatus and a cross-sectional view of thereof, respectively.
Figure 3B:
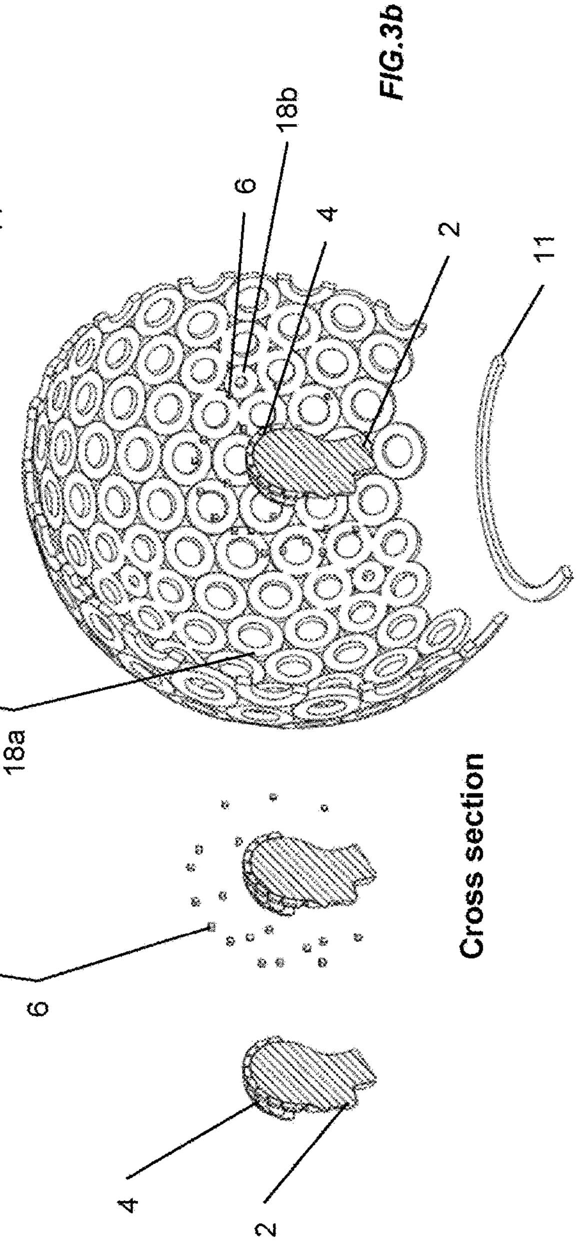

FIGS. 3*a* and 3*b* show views of a coil array that has an opening 11 for admitting the patient's head 2 (e.g., bearing a magnetoencephalography cap 4 with OPM sensors). The opening 11 is defined by the aperture of a large auxiliary coil that helps to achieve better cancelling by reducing the magnitude of the magnetic flux around the opening. The coil array can perform without such an auxiliary coil. It is noted that the array of magnetic field generating coils comprises coil elements of different coil diameters ranging from a largest could diameter 18*a* to a smallest coil diameter 18*b*. By employing a range of coil diameters, a closer packing of the coils over the notional reference spherical shell surface is possible.

Figure 4:
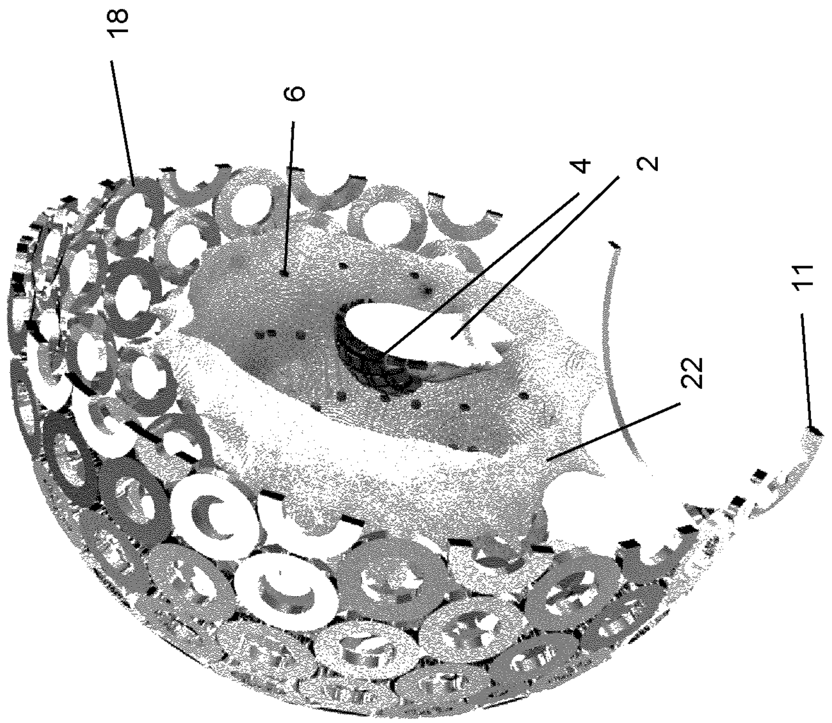
FIG. 4 shows elements of a magnetic field nulling apparatus in a cross-sectional view of thereof.

FIG. 4 shows a cross-sectional view of view of the example from the FIG. 3*b*, where a surface 22 (generated by calculation/simulation) is shown which defines the boundary of a volume in which all point within the volume have a magnetic field value of less than 5 nT. The value of 5 nT magnetic field strength therefore exists around the OPM sensors 6 and is within their dynamic range.

Figures 5A, 5B:
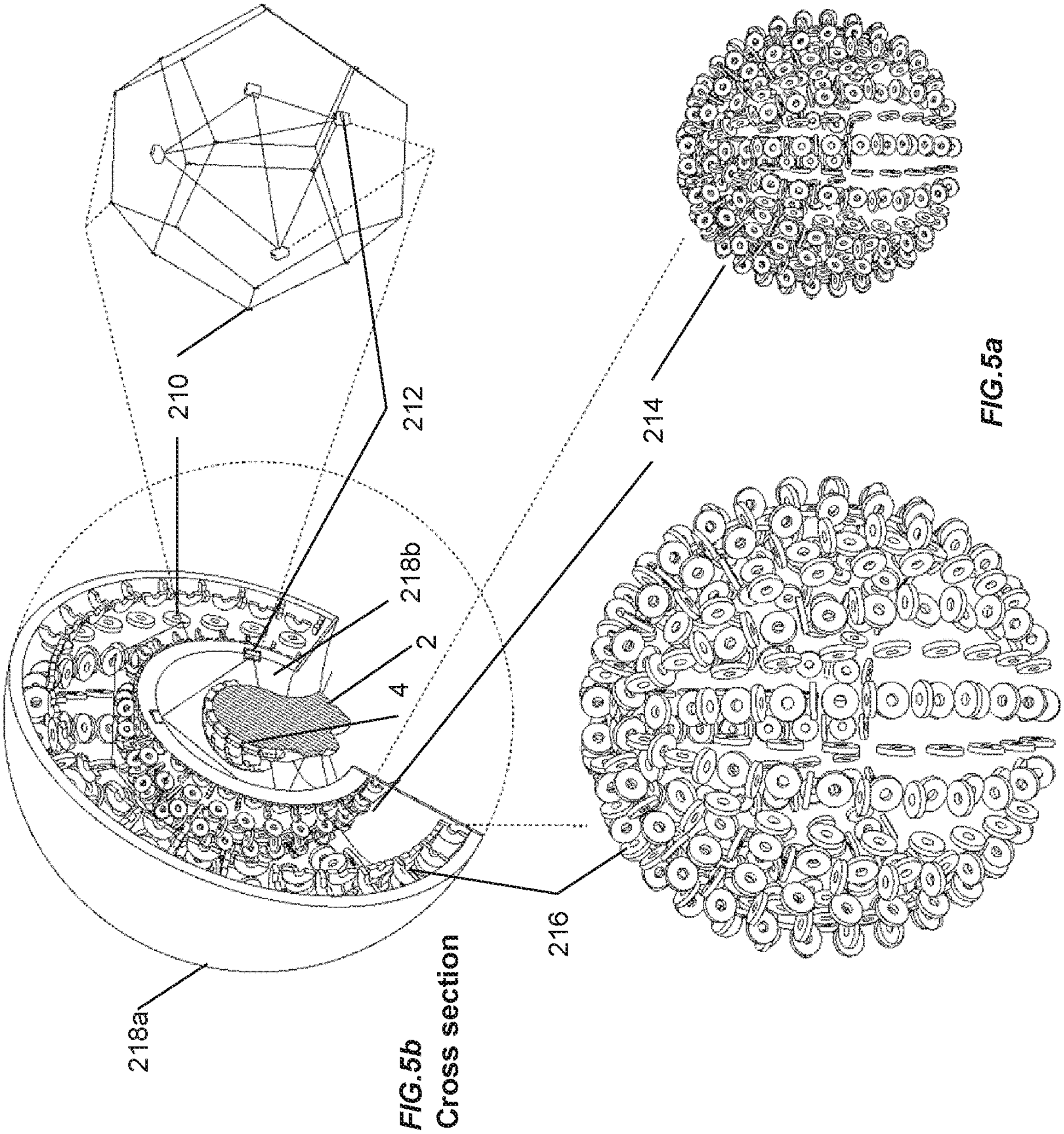
FIG. 5*a* and FIG. 5*b* show elements of a magnetic field nulling apparatus and a cross-sectional view of thereof, respectively.

A more complex version of the invention is presented on FIGS. 5*a* and 5*b*, FIG. 5*b* being a cross-sectional view of FIG. 5*a*. here, the patient 2 is wearing a MEG sensor cap. The magnetic field sensing elements 212, for example OPM sensors, are placed at a distance safe enough not to be detecting the patient's brain magnetic fields. The number these sensors is reduced, in this example, because they are associated with current control of a larger group of magnetic field generating elements 216 and 214. In particular, the array of magnetic field generating elements (coils) comprises two concentric sub-arrays of magnetic field generating elements in which an inner sub-array 214 of magnetic field generating elements is concentric with, and surrounded by, an outer sub-array 216 of magnetic field generating elements. Both the inner and outer sub-arrays are mounted upon a surface of a respective physical spherical shell support surface 218*a*, 218*b*. Both the inner and outer sub-arrays comprise magnetic field generating elements arranges regularly upon a respective notional spherical shell reference surface. Here, the coils of each sub-array of magnetic field generating elements 214, 216 comprise a plurality of sub-groups 210. Each sub-group, within each sub-array, comprises three coils each one of which faces in a respective one of three mutually perpendicular directions. The directions in which the coils of the sub-group face correspond to a local orthogonal trial (i.e., the x-y-z coordinate directions centred upon the centre of the sub-group). The direction in which any one coil of the subgroup of coils faces is a direction that is substantially perpendicular to the direction in which each of the other coils of the sub-group face such no two coils of the sub-group of coils face in the same direction. With this arrangement of sub-groups of coils, one may control the vector direction of parts of the local magnetic field in and around the region occupied by the coils of a given sub-group of coils. One coil of each sub-group of coils is configured to face in a direction towards the centre or centroid of the sub-array of magnetic field generating elements of which it forms a part.

Figure 1:
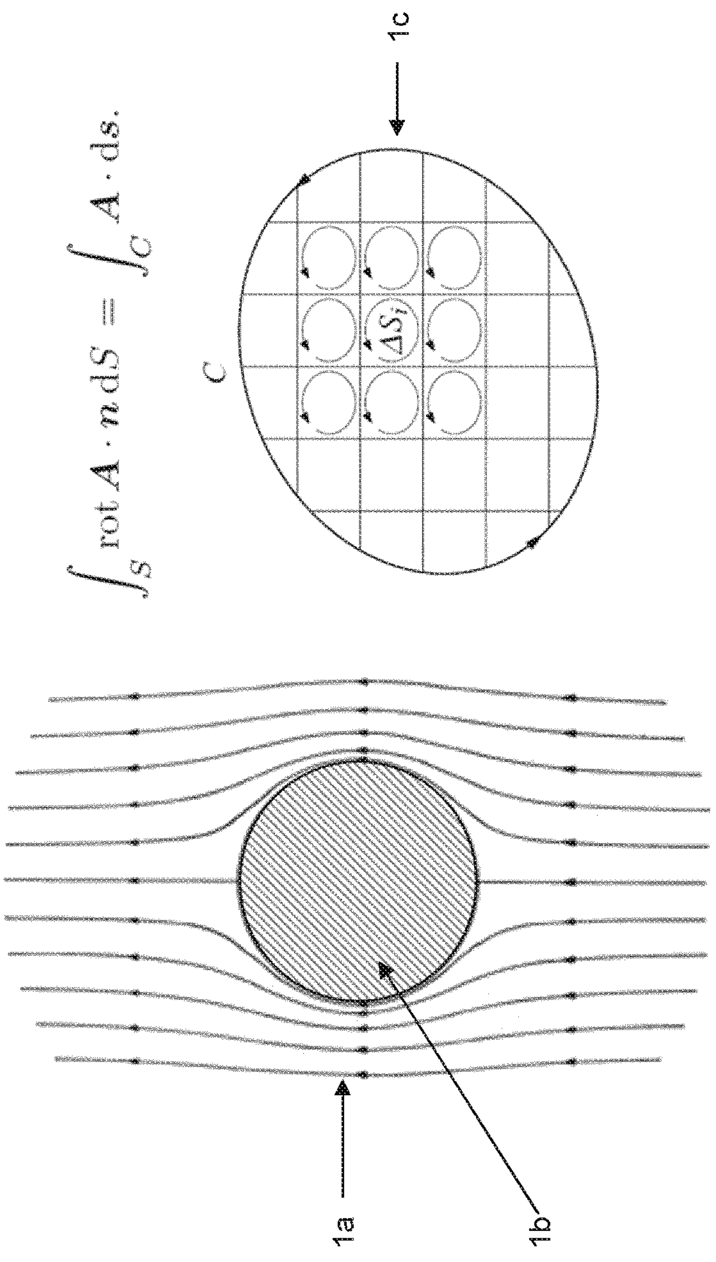
FIG. 1 shows a schematic representation of a diamagnetic effect and principles of Stokes' Theorem in 2-dimensions.
Figure 6A:
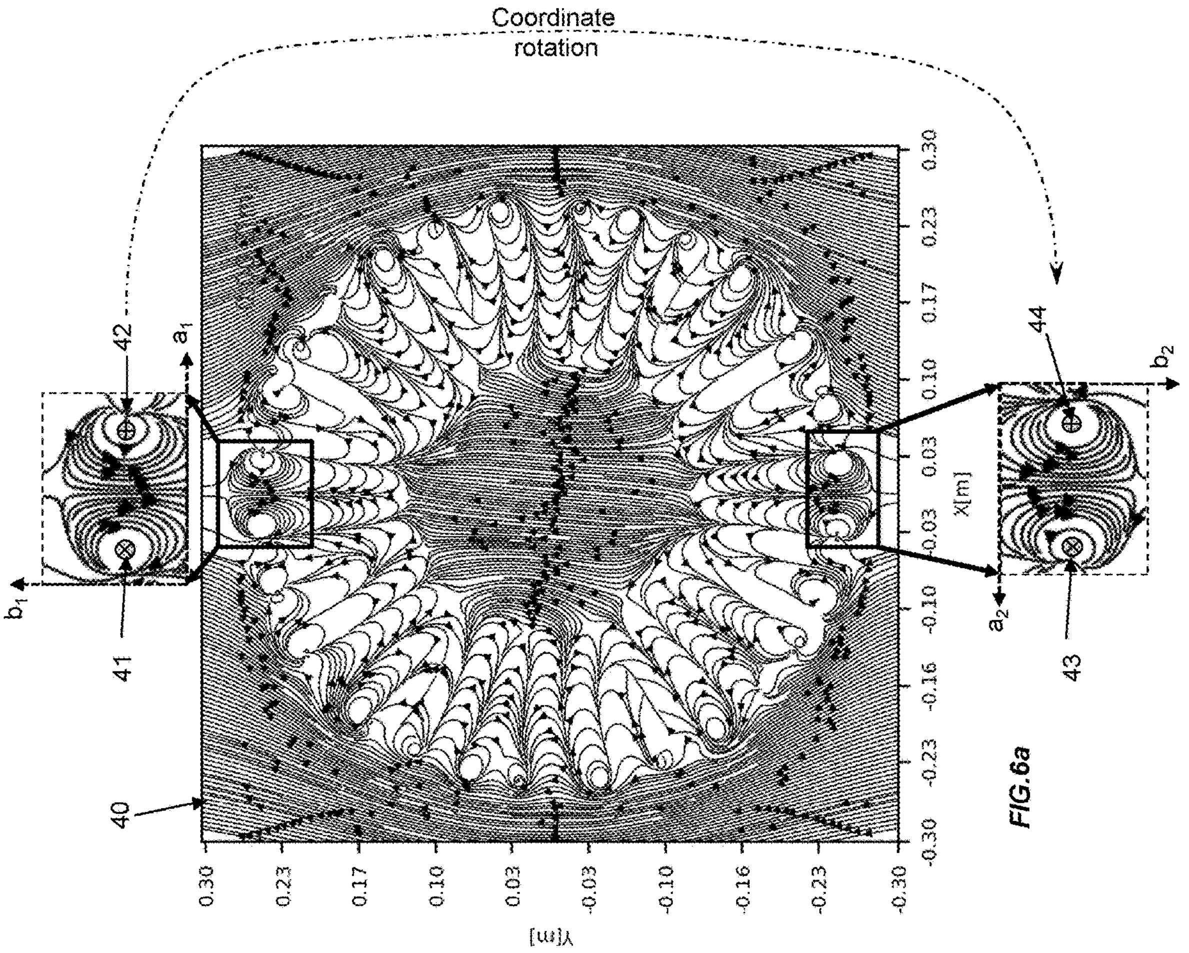
FIG. 6*a* and FIG. 6*b* show magnetic field lines representing an ambient external magnetic field and a nulling region generated by a magnetic field nulling apparatus, and a schematic representation of a diamagnetic effect, respectively.
Figure 6B:
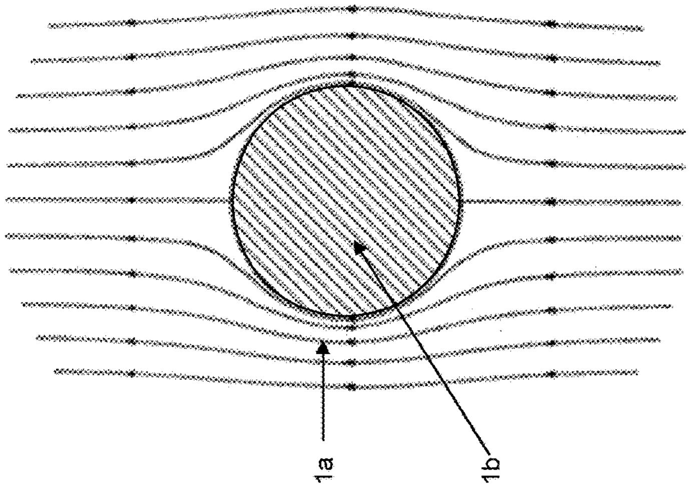

FIG. 6*b* shows an external magnetic field 1*a* passing around, but not through, a diamagnetic material 1*b* as discussed above with reference to FIG. 1. For comparison, FIG. 6*a* shows a cross-sectional view of an external magnetic field 40 (generated by calculation/simulation) passing around an array of magnetic field generating coils according to embodiments of the invention. An exploded view of the magnetic fields generated by two magnetic field generating coils of the array of coils is shown in which the two coils diametrically oppose each other across the centroid of the coil array. An upper coil of the two selected coils is located at a positive 'y' coordinate and has a local coordinate system with unit vectors ($a_1$, $b_1$), whereas a lower coil of the two selected coils is located at a positive 'y' coordinate and has a local coordinate system with unit vectors ($a_2$, $b_2$). It can be seen that the local coordinate system of the lower coil corresponds to the local coordinate system of the upper coil when the latter is rotated by about the z-axis by 180 degrees such that $a_2=-a_1$ and $b_2=-b_1$. The direction is the electrical current is indicated for each coil, with the symbol ⊗ (41, 43) indicating a current flow in the negative z-direction (i.e., into the plane of the page) and a symbol ⊕ (42, 44) indicating a current flow in the positive z-direction (i.e., out of the plane of the page). One can see that the current flows closest to the origin of coordinates in each of the two coil local coordinate systems have opposite directions indicating that the respective currents have opposite signs.

Figure 7:
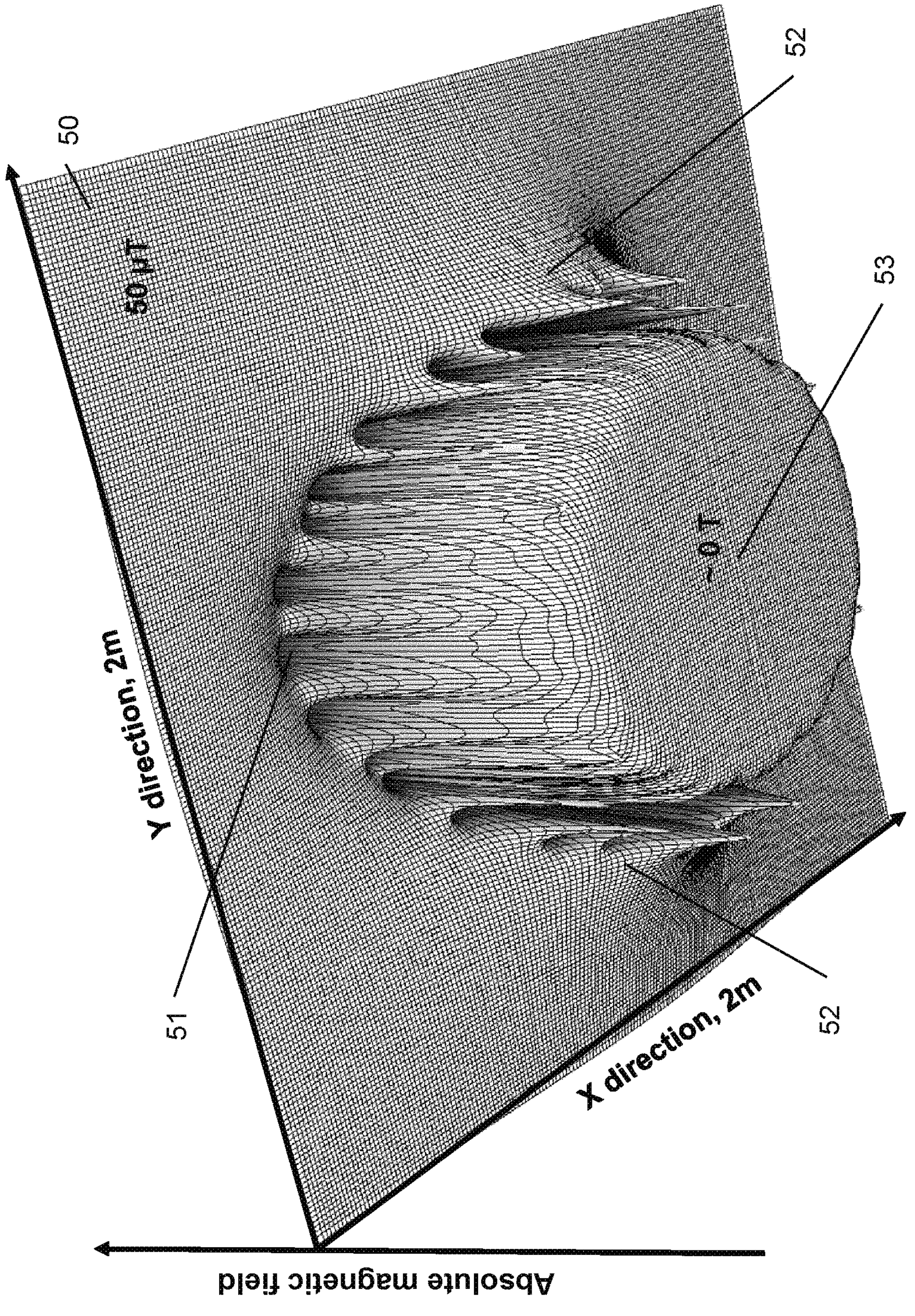
FIG. 7 shows a magnetic field strength spatial plot representing an ambient external magnetic field and e nulling region generated by a magnetic field nulling apparatus.

A 3D visualisation of a similar coil array nulling action is shown in FIG. 7 (generated by calculation/simulation) according to embodiments of the invention. The surface height in FIG. 7 represents magnetic flux density. A coil array with 252 coils was used with a diameter of 1 m in FIG. 7. A 50 μT uniform field was cancelled inside the coil to negligible values. The vector of the magnetic field was parallel to the Y axis. The cross-section through the middle of the coil array, containing the x-y plane at z=0, was taken in both FIG. 6*a* and FIG. 7. A nulled region 53 is clearly seen. A 'dent' 51, being one of several dents along the periphery of the nulled region, corresponds to the location on the surface where a magnetic field generating coil is located. This shows how large the nulled region is with the respect to the diameter of the coil array. The ambient external magnetic field 50 is shown by the surface part with 50 μT undisturbed field strength. A dip 52 of the field either side of the coil array aligned along the y-axis is a response of cancelling the action of the uniform field which is also directed along the positive y-axis.

Figure 8:
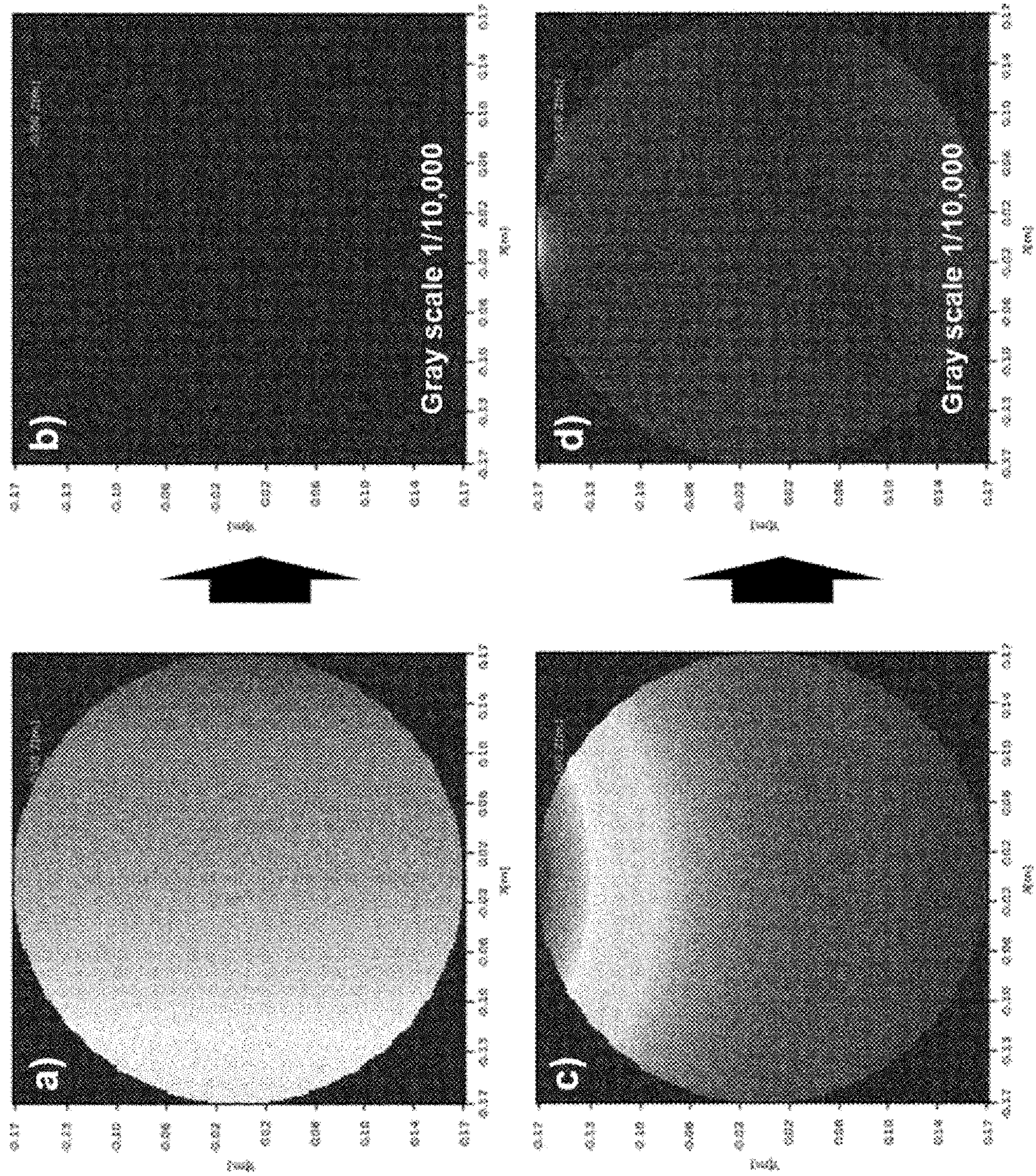
FIG. 8*a* and FIG. 8*b* and FIG. 8*c* and FIG. 8*d* show magnetic field strengths in a nulling region generated by a magnetic field nulling apparatus.

FIGS. 8*a*, 8*b*, 8*c* and 8*d* show examples (generated by calculation/simulation) of the gradient field cancelation performance of embodiments of the invention. The grey scale of FIGS. 8*a* and 8*c* is enhanced by a factor of 10,000 in FIGS. 8*b* and 8*d*, respectively. The results of FIG. 8*a* correspond to an ambient external magnetic field gradient source in with a magnetic field directed in the positive x-axis direction of the figure. FIG. 8*b* is the result of nulling/cancelling the field of FIG. 8*a*. The lack of white colour shows that the magnetic field from the source was reduced more than 10,000 times. The results of FIG. 8*c* correspond to an ambient external magnetic field gradient source in with a magnetic field directed in the positive y-axis direction of the figure. FIG. 8*d* is the result of nulling/cancelling the field of FIG. 8*c*. The lack of white colour shows that the magnetic field from the source was reduced more than 10,000 times.

Figure 9:
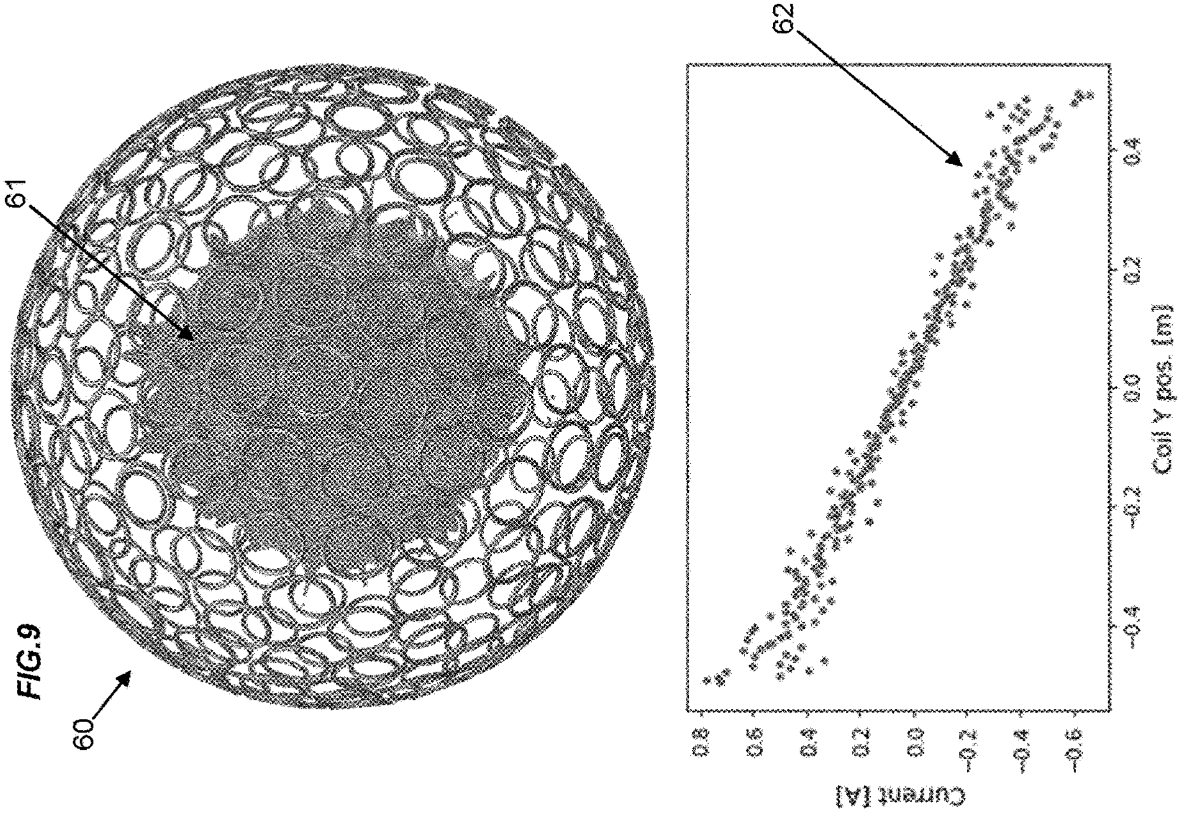
FIG. 9 shows a view of an array of magnetic field generating elements of a magnetic field nulling apparatus, and a nulled region therein, together with a plot of electrical current values applied to magnetic field generating elements of the magnetic field nulling apparatus for achieving the nulled region.

FIG. 9 shows a magnetic field generating coil array 60 in which the locations of each coil define a Fibonacci lattice. The array comprises 252 coils forming an array of 1 m diameter. The 3D shape 61 (generated by calculation/simulation) inside the col array indicates a region with magnetic field lower than 5 nT, providing nulling/cancellation against a uniform external ambient (e.g., Earth's) magnetic field of 50 μT directed along the y-axis passing from left to right in the figure. The magnitude and relative direction (positive/negative) if the drive currents 62 applied to coils of this array of coils is shown with respect to the y-coordinate value of the respective coils. Here the y-axis passes from left to right in the figure and the centre of coordinates corresponds to the centre of the array of coils.

Figure 10:
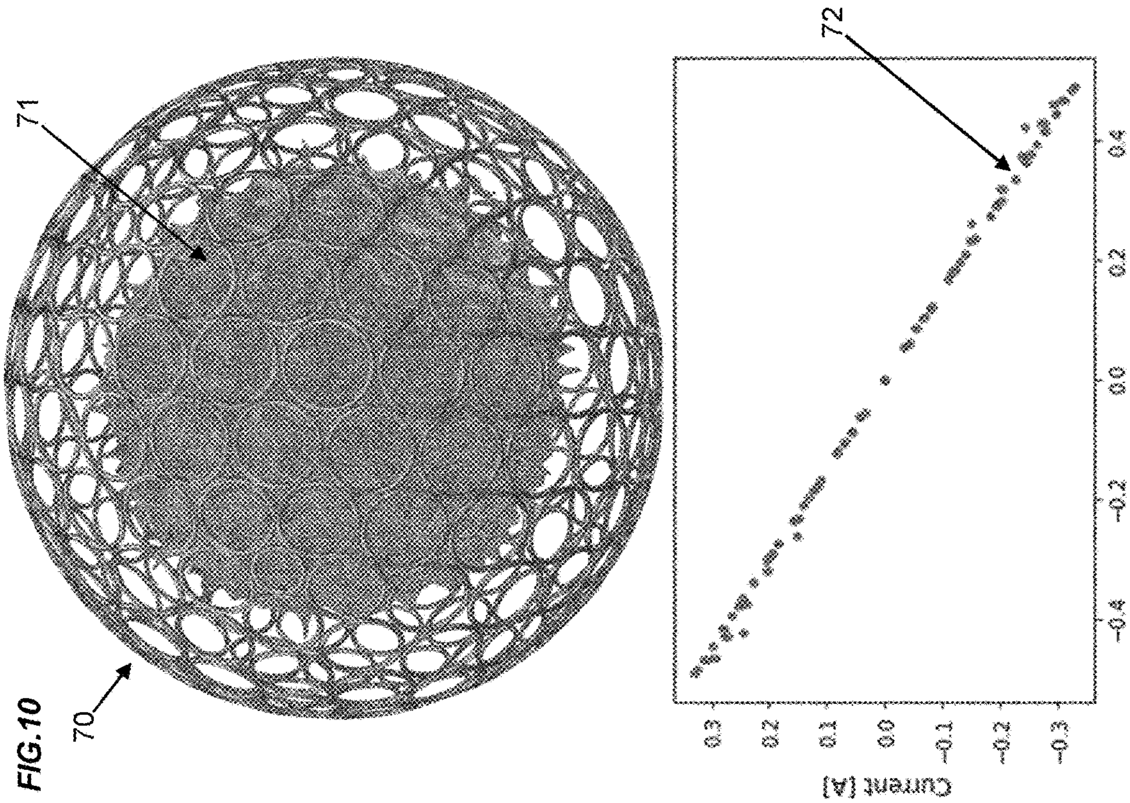
FIG. 10 shows a view of an array of magnetic field generating elements of a magnetic field nulling apparatus, and a nulled region therein, together with a plot of electrical current values applied to magnetic field generating elements of the magnetic field nulling apparatus for achieving the nulled region.

FIG. 10 shows a magnetic field generating coil array 70 in which the locations of each coil define a Dual Geodesic Icosahedron lattice. The array comprises 252 coils forming an array of 1 m diameter. The 3D shape 71 (generated by calculation/simulation) inside the col array indicates a region with magnetic field lower than 5 nT, providing nulling/cancellation against a uniform external ambient (e.g., Earth's) magnetic field of 50 μT directed along the y-axis passing from left to right in the figure. The magnitude and relative direction (positive/negative) if the drive currents 72 applied to coils of this array of coils is shown with respect to the y-coordinate value of the respective coils. Here the y-axis passes from left to right in the figure and the centre of coordinates corresponds to the centre of the array of coils. Note that approximately 50% lower currents are required in the Dual Geodesic Icosahedron lattice as compared to the Fibonacci lattice. Table 1 shows a comparison of performance parameters for these two coil arrays.

TABLE 1

| 252 coils | Dual Geodesic Icosahedron | Fibonacci |
|---|---|---|
| Max. B-field [nT] | 0.01 | 0.23 |
| Avg. B-field [nT] | 0.008 | 0.036 |
| Max. Gradient [nT/cm] | 0.0002 | 0.035 |
| Avg. Gradiant [nT/cm] | 0.00007 | 0.0022 |

Figure 11:
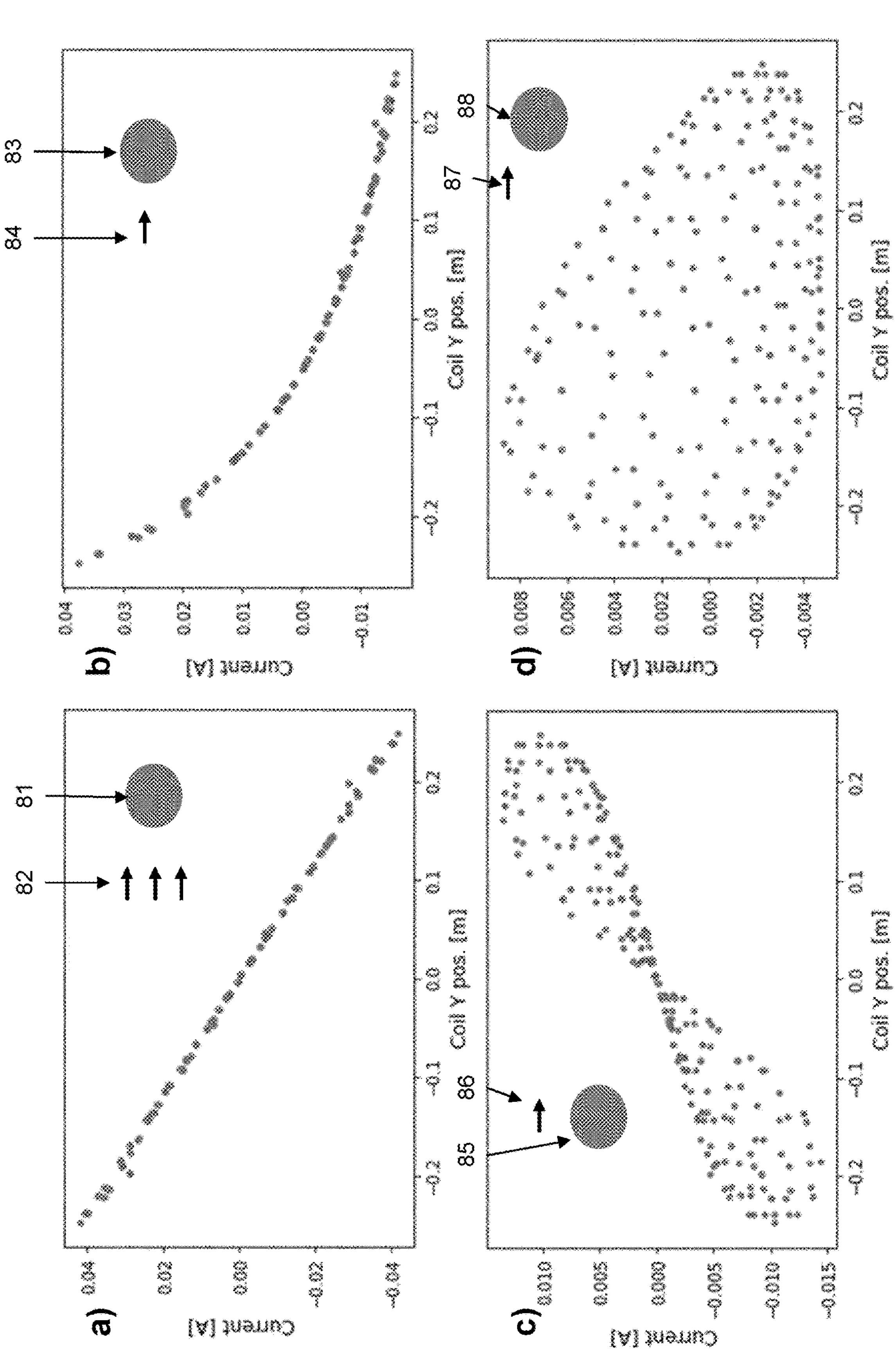
FIGS. 11*a* to 11*d* show plots of electrical current values applied to magnetic field generating elements of a magnetic field nulling apparatus for achieving a nulled region.

FIGS. 11*a*, 11*b*, 11*c* and 11*d* show other examples (generated by calculation/simulation) of drive currents applied to a spherical array of magnetic field generating coils as a function of the coordinate value of the given coil along the y-axis. In each case, the coil array lattice (81, 83, 85, 88) is a Dual Geodesic Icosahedron array with 212 coils. Arrows 82, 84, 86 and 87 represent different magnetic field distributions/sources. The magnetic field vector to be cancelled is parallel to y-axis. FIG. 11*a* corresponds to a uniform magnetic field (3 arrows 82). The drive current delivered to each coil of the array, to achieve nulling, is almost perfectly linearly proportional to the y-axis position coordinate of the given coil. FIG. 11*b* corresponds to a point magnetic field (1 arrow 84) lying on the negative y-axis. The linearity between the drive current and coil y-coordinate of FIG. 11*a* is now replaced by a bend. FIG. 11*c* corresponds to a point magnetic field 86 located on the positive x-axis, but directed parallel to the positive y-axis. FIG. 11*d* corresponds to a point magnetic field 87 located at a positive x-coordinate and a negative y-coordinate, but directed parallel to the positive y-axis.

Figure 12:
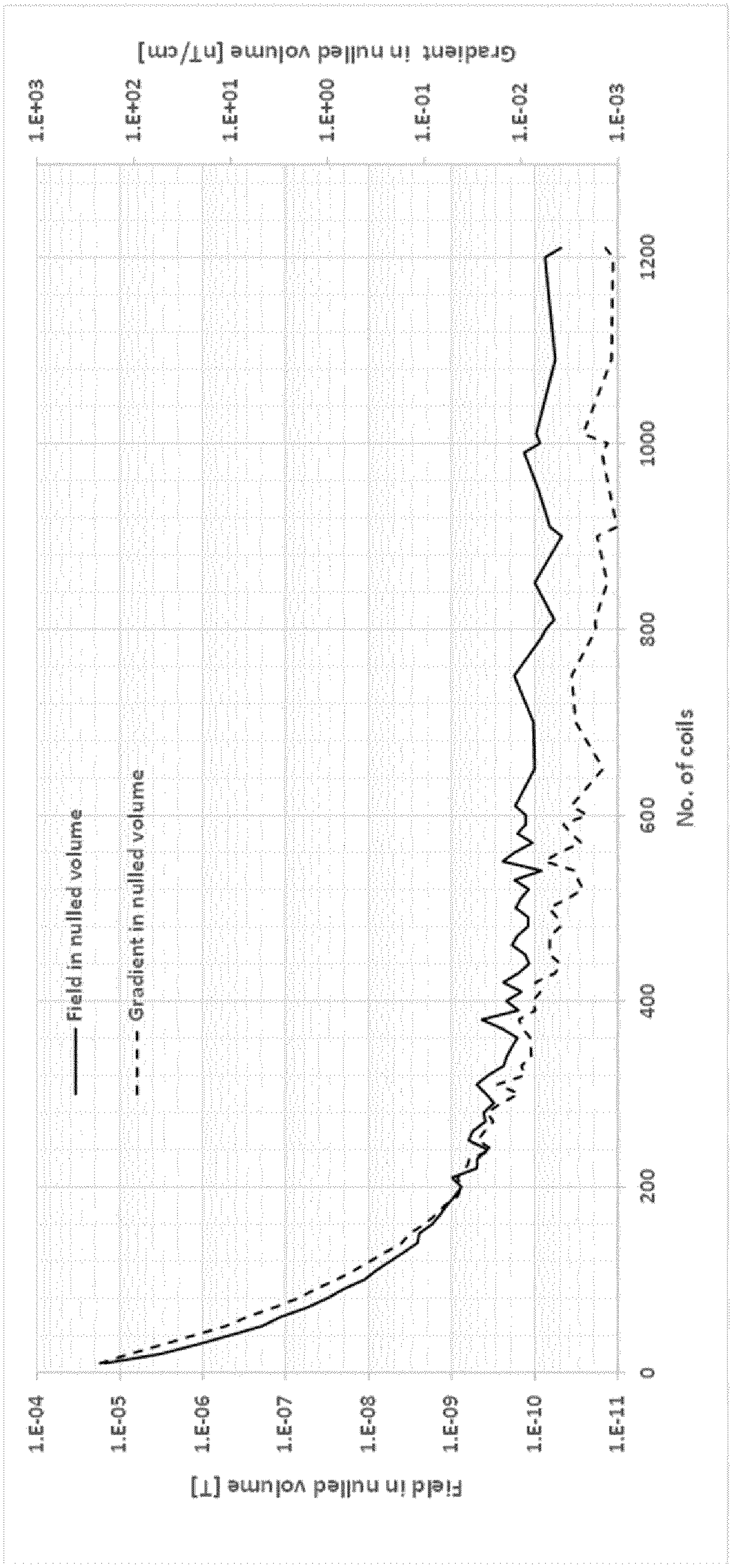
FIG. 12 shows plots of magnetic field strength and magnetic field gradient generated by a magnetic field nulling apparatus within the nulling region thereof, as a function of varying numbers of magnetic field generating elements provided within the magnetic field nulling apparatus.
Figure 13:
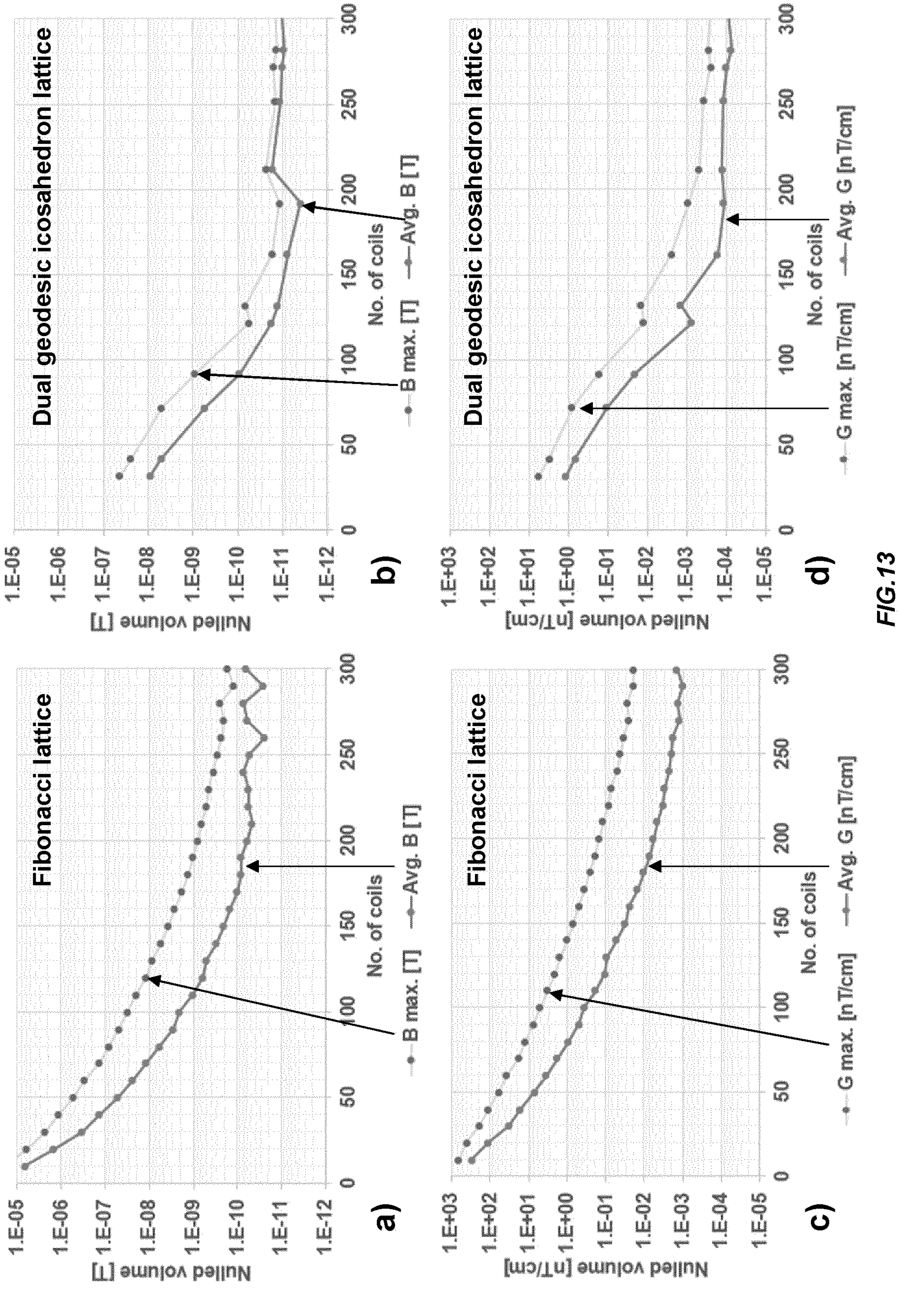
FIGS. 13*a* to 13*d* show plots of average magnetic field strength and maximum magnetic field strength, as well as plots of average magnetic field gradient and maximum magnetic field gradient generated by a magnetic field nulling apparatus within the nulling region thereof, as a function of varying numbers of magnetic field generating elements provided within the magnetic field nulling apparatus and for different lattice types.

FIG. 12 shows typical values (generated by calculation/simulation) of the magnetic field value and magnetic field gradient achieved within the nulling region of examples of the invention, as a function of the number of magnetic field generating coils of the Fibonacci lattice array in question. FIGS. 13*a*, 13*b*, 13*c* and 13*d* show further examples of this in respect of a Fibonacci lattice (FIG. 13*a*—field value; FIG. 13*c*—field gradient) and a Dual Geodesic Icosahedron lattice (FIG. 13*b*—field value; FIG. 13*d*—gradient). In each case, both the maximum value and the average value, of either the field value or field gradient, are shown. These figures show how the performance of the coil array improves when number of coils is increased, and also show that lattice type has significant influence. The coil array diameter was 1 m and was working against uniform 50 μT field. The assessed region was a sphere with 0.35 diameter.

It is shown that use of Dual Geodesic Icosahedron lattice has better performance than use of Fibonacci lattice.

Figure 14B:
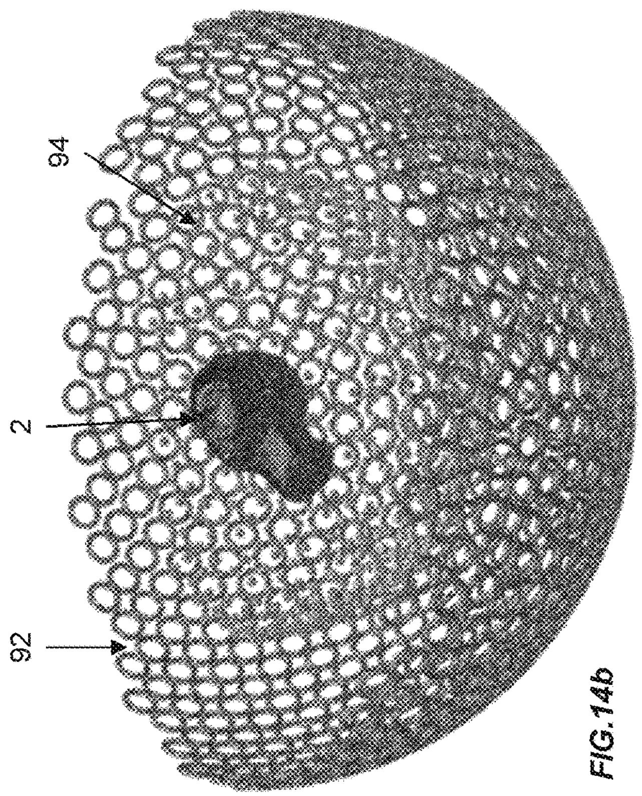
FIGS. 14*a* and 14*b* show cross-sectional views of an array of magnetic field generating elements of a magnetic field nulling apparatus each comprising a respective one of two different arrays of magnetic field sensing elements of a magnetic field nulling apparatus.
Figure 14A:
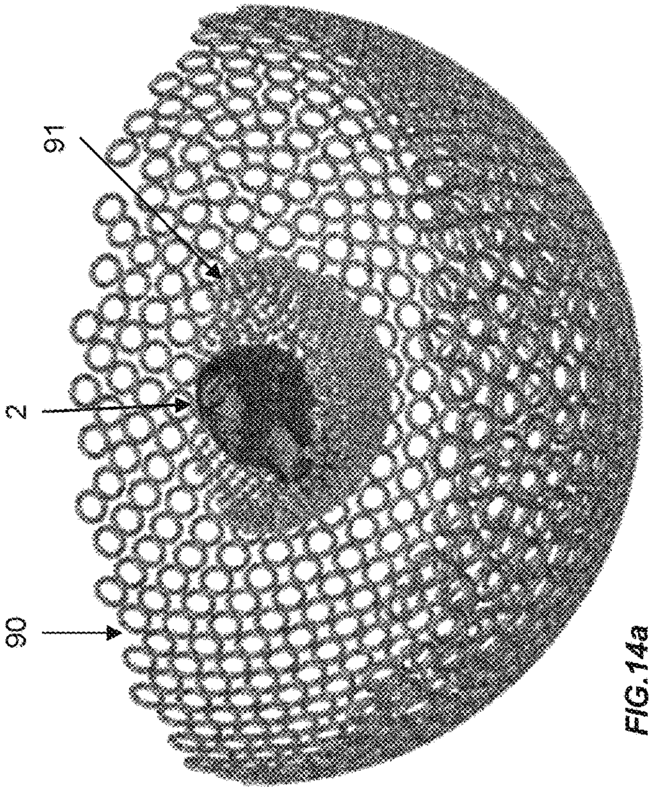

FIGS. 14*a* and 14*b* show cut-away views of a spherical shell array of magnetic field generating coils (90, 92) surrounding a spherical shell array of magnetic field sensing elements (91, 94) which is configured to be substantially concentric with the array of magnetic field generating coils surrounding it. A patient's head 2 is located at the centre of the array of magnetic field sensing elements. The inventors have found that this concentric arrangement permits particularly accurate and effective nulling within a nulling region. The separate respective locations of coils (91, 92) of the coil arrays and of sensors in the sensor array (91, 94) are each defined according to a regular respective lattice, with the locations in question coinciding with (or be defined by) notional vertices or facets of a polyhedron or points on a spherical surface. A respective one of two physical polyhedral or spherical support structures (not shown) supports the elements of each respective array at these locations. The plurality of magnetic field generating coils (90, 92) are arranged at said separate respective locations substantially equidistant from the centre of the nulling region thereby defining a substantially spherical array surrounding the nulling region. Similarly, the plurality of magnetic field sensing elements (91, 94) are also arranged at separate respective locations substantially equidistant from the centre of the nulling region thereby also defining a substantially spherical array which is within the nulling region.

FIG. 14*a* shows cross-sectional view of an apparatus in which the diameter (sensors spherical array diameter of 0.35 m) of the array of magnetic field sensing elements 91 relative to the diameter (coils spherical array diameter of 1.0 m) of the array 90 of magnetic field generating coils, is smaller than the diameter (sensors spherical array diameter of 0.61 m) of the array of magnetic field sensing elements 94 relative to the diameter (coils spherical array diameter of 1.0 m) of the array 92 of magnetic field generating coils of the apparatus shown in cross-section in FIG. 14*b*. The inventors have found that an optimum position (e.g., array diameter) exists for the sensors to be positioned within the surrounding coil array at which performance dramatically improves. The optimum position is found to depend upon the coil array diameter, number of coils in the coil array, lattice type defining the coil array, and the shape of the coils. For example, it had been found that for a Fibonacci lattice with 1200 coils as shown in FIG. 14*a* and FIG. 14*b*, the optimum positions of the sensors of the sensor array, when the sensor array is a spherical shell array, corresponds to an array with a concentric diameter which is 0.61 times the diameter of the surrounding coil array, as shown in FIG. 14*b*.

Figure 15B:
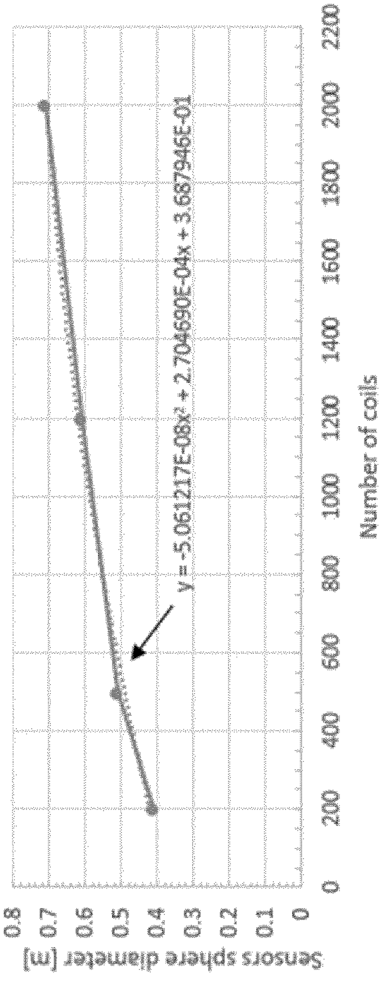
FIG. 15*b* shows a plot of the optimal diameter of the concentric spherical array of magnetic field sensing elements as a function of the number of magnetic field generating elements within the spherical array of magnetic field generating elements to which FIG. 16*a* relates.
Figure 15A:
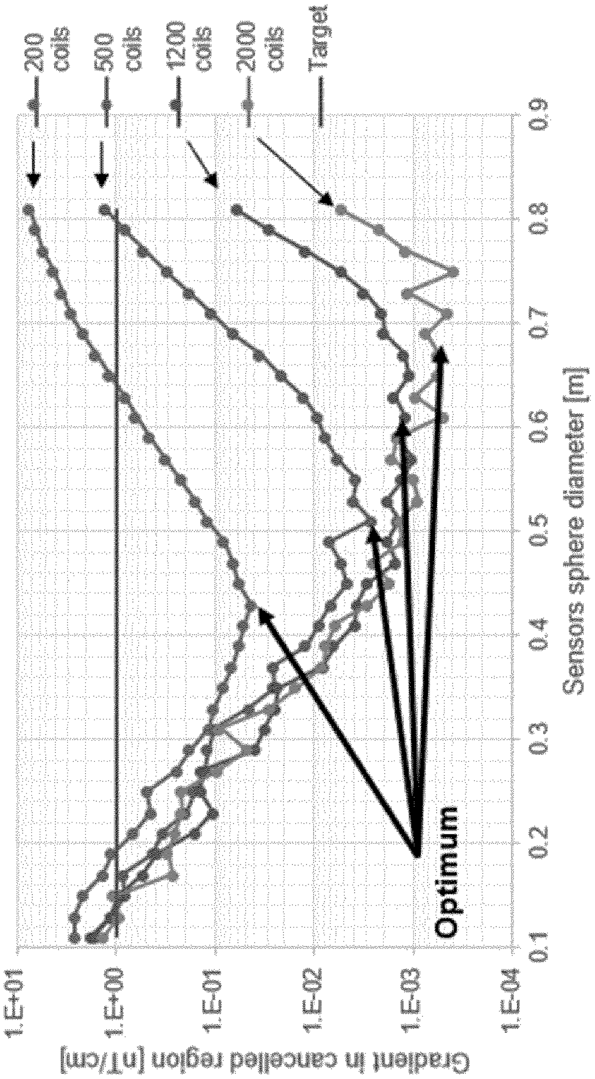
FIG. 15*a* shows plots of magnetic field gradient achieved within a nulling region of a spherical array of magnetic field generating elements of a magnetic field nulling apparatus, as a function of varying diameter of a concentric spherical array of magnetic field sensing elements within the array of magnetic field generating elements.

Generally, optimal sensor positions correspond with sensor array concentric diameters with values in the range if at least about 30% to 90% of the diameter of the array of magnetic field generating coils surrounding them. FIGS. 15*a* and 15*b* show how the value of the magnetic field gradient in the nulled region of an external ambient magnetic field (FIG. 15*a*) varies as a function of the diameter of the array of magnetic field sensors (the coil array diameter was fixed), and the variation of the optimal sensor array diameter (FIG. 15*b*) as a function of the number of coils in the array (the coil array diameter was varied). Here, the coil array is a Fibonacci lattice. For example, when 2000 coils are used, the nulled magnetic field is field below 1.6 μT in the nulled volume when the sensor array diameter is about 68% of the diameter of the coil array, and this nulled field value rises to only 0.95 nT when the diameter of the sensor sphere is increased to about 0.81% of the coil array diameter: that example means that with use of a 1 m diameter coil array sphere, the sensor array sphere has 0.81 m diameter. FIG. 15*b* shows how the value of the optimal sensor array sphere diameter changes as a function of variations in the number of magnetic field generating coils employed in spherical Fibonacci array of coils. The relationship is quadratic to a good approximation, with the sensor array diameter varying as a quadratic function of the number of coils in the coil array.

Figure 16:
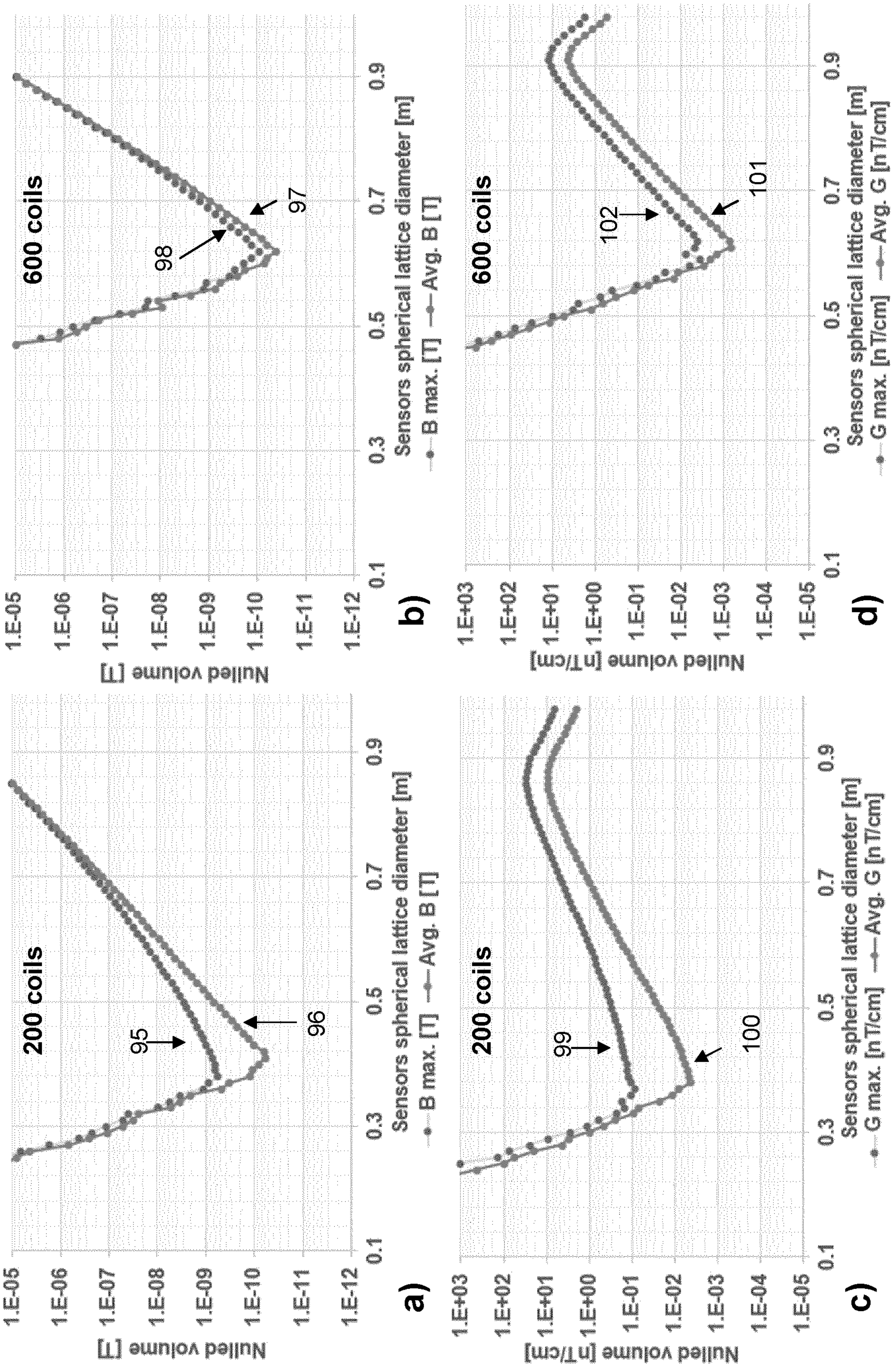
FIGS. 16*a* to 16*d* show plots of the average magnetic field strength and maximum magnetic field strength, as well as plots of average magnetic field gradient and maximum magnetic field gradient, generated by a magnetic field nulling apparatus within the nulling region thereof, as a function of varying diameter of a concentric spherical array of magnetic field sensing elements within the array of magnetic field generating elements of the magnetic field nulling apparatus.
Figure 17:
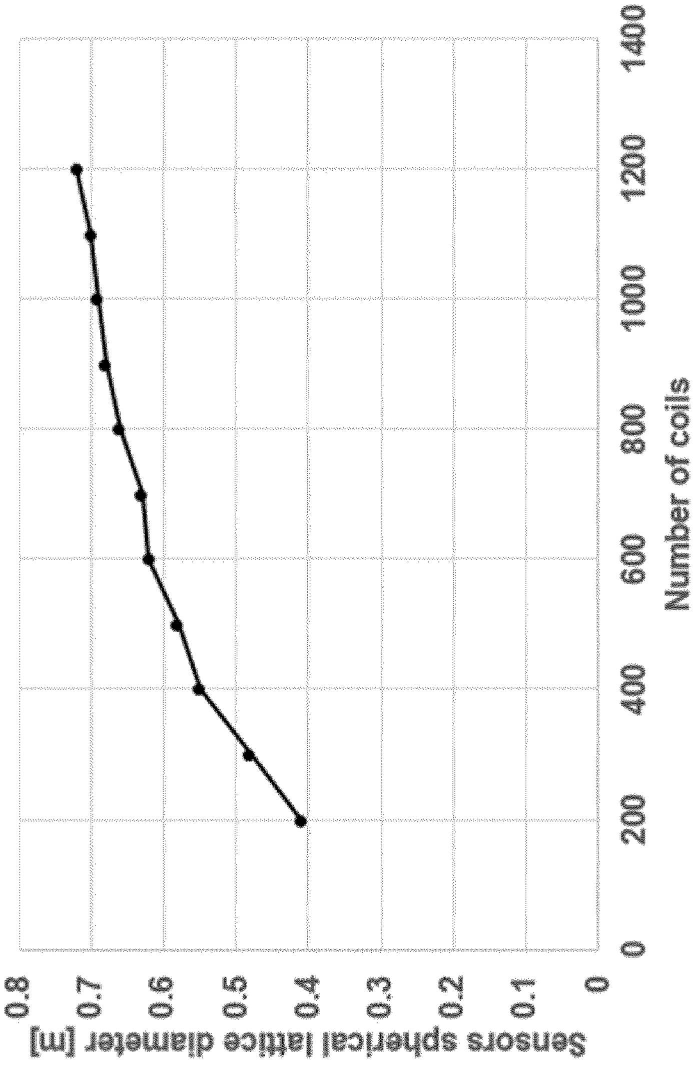
FIG. 17 shows a plot of the optimal diameter of the concentric spherical array of magnetic field sensing elements as a function of the number of magnetic field generating elements within the spherical array of magnetic field generating elements to which FIGS. 16*a* to 16*d* relate.

FIGS. 16*a* and 16*c* show further examples of how the value of the magnetic field (FIG. 16*a*) and magnetic field gradient (FIG. 16*c*) in the nulled region of a 200-coil array within an external ambient magnetic field, varies as a function of the diameter of the array of magnetic field sensors when the diameter of the coil array is a Fibonacci lattice fixed at 1.0 m diameter and the ambient magnetic field being nulled is a uniform 50 μT field. Both the maximum value 95 and average value 96 of the magnetic field are shown, as well as the maximum value 95 and average value 100 of the magnetic field gradient. FIGS. 16*b* and 16*d* show further examples of how the value of the magnetic field (FIG. 16*b*) and magnetic field gradient (FIG. 16*d*) in the nulled region of a 600-coil array within an external ambient magnetic field, varies as a function of the diameter of the array of magnetic field sensors when the diameter of the coil array is Dual Geodesic Icosahedron lattice fixed at 1.0 m diameter and the ambient magnetic field being nulled is a uniform 50 μT field. Both the maximum value 98 and average value 97 of the magnetic field are shown, as well as the maximum value 102 and average value 101 of the magnetic field gradient. It is clearly seen that optimal sensor array diameters exist in each case, corresponding to minimal magnetic field and field gradient values. FIG. 17 shows how the value of the optimal sensor array sphere diameters identified from FIGS. 16*a*-16*d* change as a function of variations in the number of magnetic field generating coils employed in spherical Fibonacci array of coils. The relationship is quadratic to a good approximation, with the sensor array diameter varying as a quadratic function of the number of coils in the coil array.

Consequently, the inventors have discovered a strong synergy between the diameter of the array of magnetic field generating elements and the diameter of the array of magnetic field sensing elements necessary to achieve optimal nulling of the magnetic field within the nulling region. In other words, by optimally placing the sensors of the feed-back system of the invention, optimal feed-back values of the magnetic field are delivered to the control system to optimally control the electrical currents used to drive the magnetic field generating elements in reducing the magnetic field within the nulling region. The size of a diameter of the array of magnetic field sensing elements is preferably between about 40% and about 80% of the size of a diameter of the array of magnetic field generating elements. For example, the size of a diameter of the array of magnetic field sensing elements may be between about 40% and about 90% of the size of a diameter of the array of magnetic field generating elements and the array of magnetic field generating elements comprises more at least about 200 elements and not more than about 2000 elements. The inventors have found that especially effective field nulling may be achieved when one or more of these conditions is applied.

Figure 18:
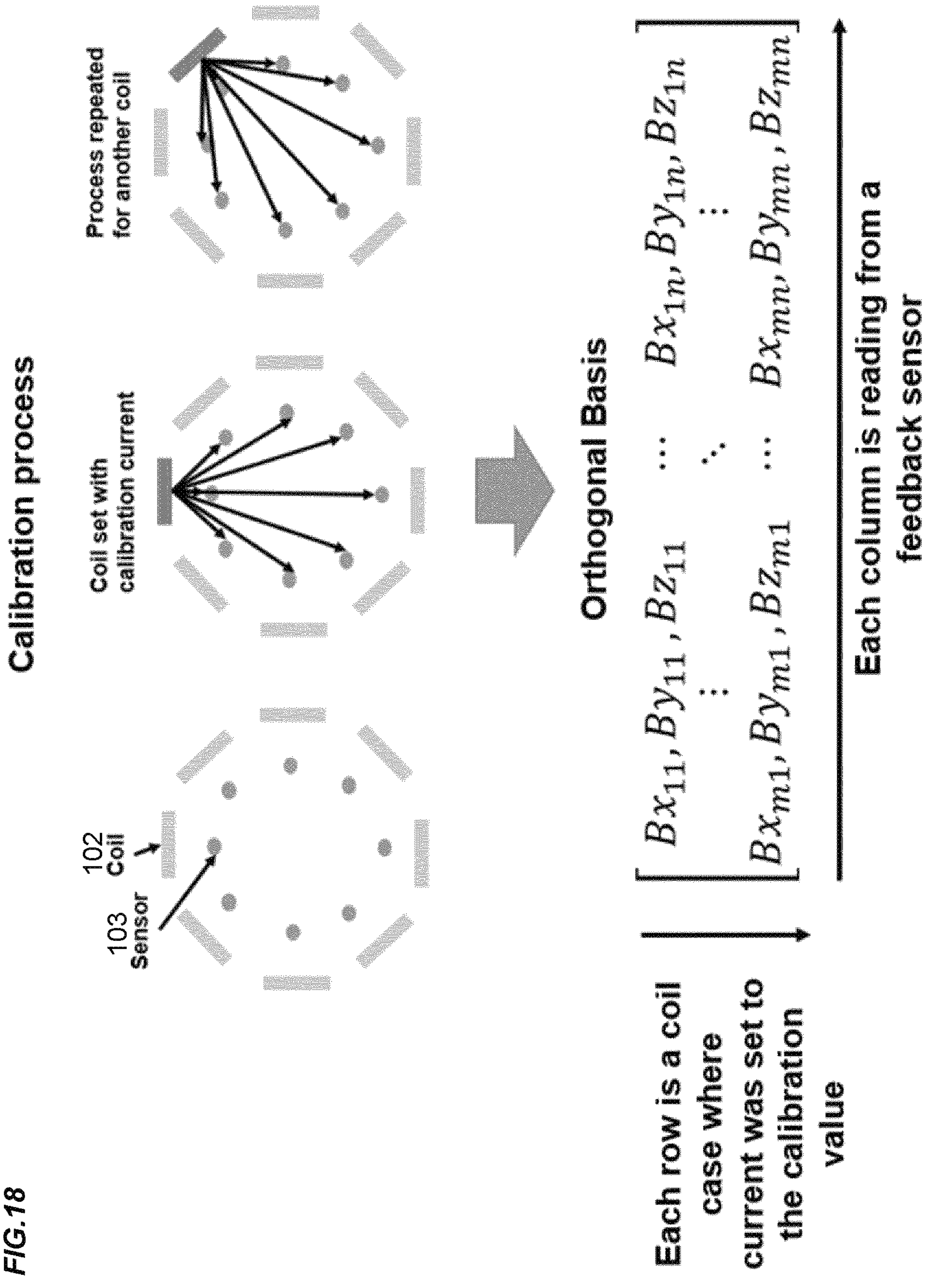
FIG. 18 shows schematically a process for calculating the electrical current to be applied to an array of magnetic field generating elements using measurements from array of magnetic field sensing elements.
Figure 19:
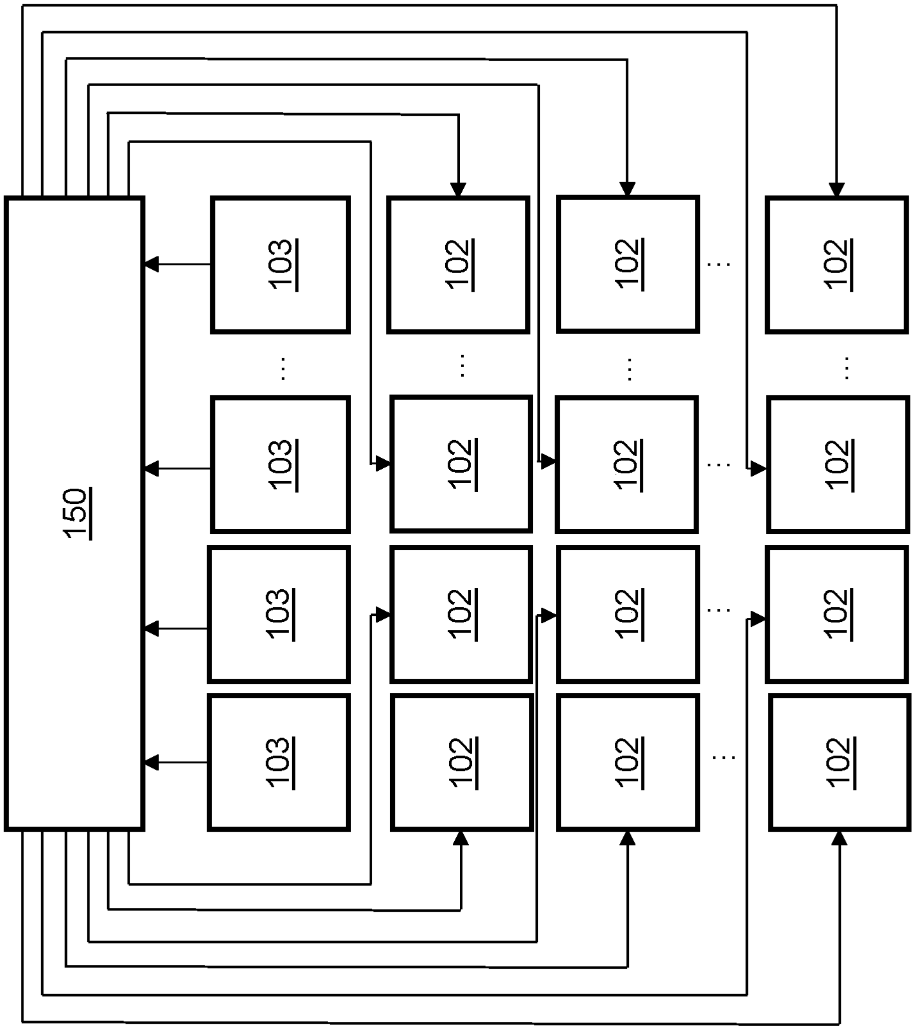
FIG. 19 shows schematically the elements of a magnetic field nulling apparatus.
Figure 21C:
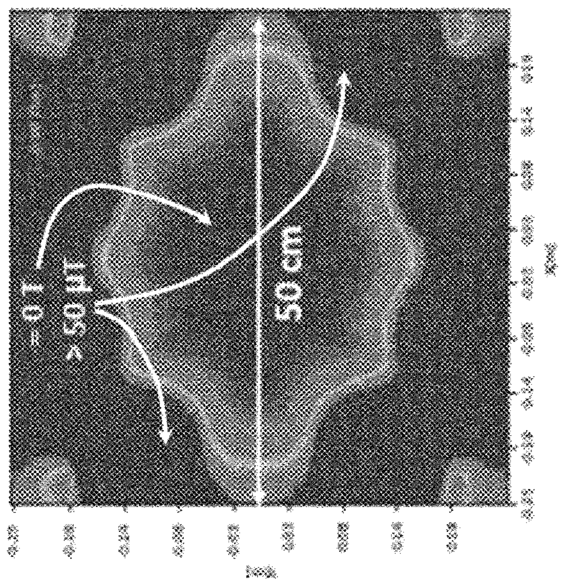
FIGS. 21*a* to 21*c* show plots of the magnetic field nulling generated by the process of FIG. 18.
Figure 21B:
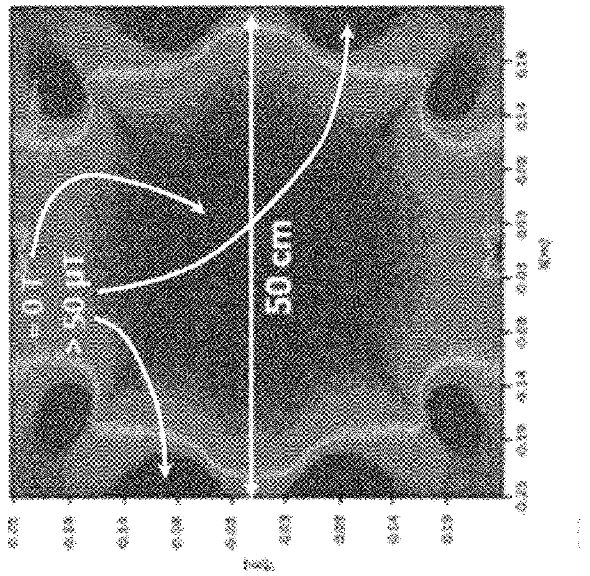
Figure 21A:
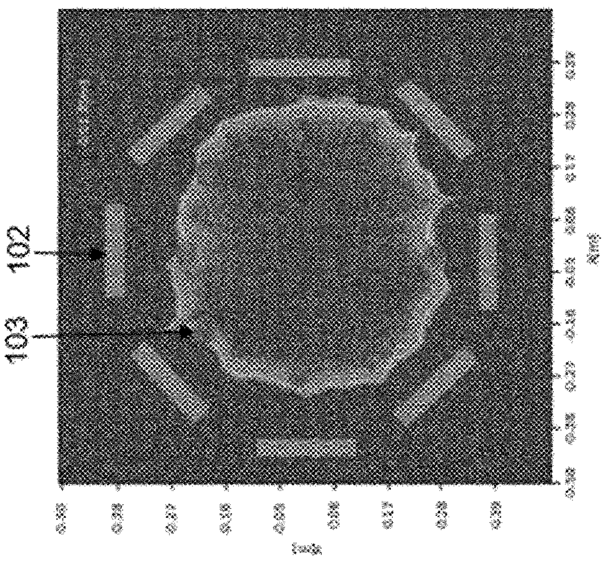

FIG. 18 schematically shows a process for determining the values of electrical currents to be supplied to magnetic field generating coils of the coil array. FIG. 19 shows an apparatus for nulling a magnetic field within a nulling region in an external ambient magnetic field comprising a plurality of separate magnetic field generating elements 102 placed at separate respective locations surrounding the nulling region for generating respective nulling magnetic fields extending into the nulling region. A plurality of magnetic field sensing elements 103 are placed at a plurality of respective separate locations within the nulling region for sensing respective values of the magnetic field within the nulling region. A feedback control unit 150 is configured for controlling the values of the respective nulling magnetic fields generated by each of the plurality of magnetic field generating elements in response to values of the magnetic field sensed by the plurality of magnetic field sensing elements. The feed-back control unit is arranged to drive the magnetic field generating elements 102 with respective electric currents that reduce the magnetic field values detected by respective magnetic field sensing elements 103 to values not exceeding a pre-set threshold value corresponding to a pre-set nulling of the magnetic field within the nulling region.

The feed-back control unit is arranged to calculate the appropriate driving currents as follows. Consider following items:

Minimisation of magnetic field readings in sensors 103 is enough to get cancelled field inside targeted nulling volume.

A magnetic field reading on a sensor 103 is the sum of all magnetic fields from all of the magnetic field generating elements 102 and the external ambient field combined.

Each sensor of coil position is fixed by this spatial component of the magnetic field equation is constant.

The only variable that is changing is the drive current that has a proportional dependence to the magnetic field.

The contribution of each magnetic field generating elements 102 (e.g., coil) to all sensors 103 can be calibrated. When magnetic field is cancelled then so too is the feedback value of the magnetic field sensed by the sensors for the volume being surrounded by these sensors. There is a proportional dependence between current and magnetic field. The following equations describe the magnetic field value at a given location which is a fixed location for each sensor expressed in cylindrical coordinates:

$$B_\rho(\rho, z) = \frac{\mu_0 NI}{2\pi}\frac{z}{\rho\left[(a+\rho)^2+z^2\right]^{1/2}}\left[-K(k)+\frac{a^2+\rho^2+z^2}{(a-\rho)^2+z^2}E(k)\right]$$

$$B_z(\rho, z) = \frac{\mu_0 NI}{2\pi}\frac{1}{\left[(a+\rho)^2+z^2\right]^{1/2}}\left[K(k)+\frac{a^2-\rho^2-z^2}{(a-\rho)^2+z^2}E(k)\right]$$

$$k = \sqrt{\frac{4a\rho}{(a+\rho)^2+z^2}}$$

Here:

a=the radial distance from the axis of the cylindrical coordinate system.

z=the distance along the axis of the cylindrical coordinate system.

ρ=radius of the turn of a coil.

$\mu_o$=permeability of free space.

K(k)=an elliptic integral of the 1st kind.

E(k)=an elliptic integral of the 2nd kind.

In other words, each coil in turn is driven by an electric current alone while all other coils receive no drive current at all. The magnetic field generated by the lone coil is sensed by each of the magnetic field sensing elements 103 at their respective fixed locations within the nulling region. These measured field values are calibration values and define a basis vector for the lone coil in question. They are input from the respective magnetic field sensing elements 103 to the control unit 150 which stores them. The control unit is configured to repeat this process separately for each magnetic field generating coil 102 of the array of coils whereby each coil 102 takes the role of being the lone coil driven by an electric current. For each coil 102, the control unit 150 constructs a basis vector containing calibration magnetic field values for all n sensors 103. For a first coil it will be:

$$[Bx_{11}, By_{11}, Bz_{11}, \ \ldots \ Bx_{1n}, By_{1n}, Bz_{1n}]$$

The array of m coils results in an array of these basis vectors constructed using the respective basis vectors for all m coils:

$$\begin{bmatrix} Bx_{11}, By_{11}, Bz_{11} & \cdots & Bx_{1n}, By_{1n}, Bz_{1n} \\ \vdots & \ddots & \vdots \\ Bx_{m1}, By_{m1}, Bz_{m1} & \cdots & Bx_{mn}, By_{mn}, Bz_{mn} \end{bmatrix}$$

Each measurement of a magnetic field with all sensors subsequently operating in the active cancellation cycle can be written as a pseudo-vector type construct:

$$[Sx_1, Sy_1, Sz_1 \ \ldots \ Sx_n, Sy_n, Sz_n]$$

Making:

$$N = 3n,\ M = 3m$$

$$Bx_{11}, By_{11}, Bz_{11}, Bx_{12}, By_{12}, Bz_{12} \ldots = X_{11}, X_{12}, X_{13}, X_{14}, X_{15}, X_{16} \ldots$$

$$Sx_1, Sy_1, Sz_1, Sx_2, Sy_2, Sz_2 \ldots = V_1, V_2, V_3, V_4, V_5, V_6 \ldots$$

The equation for orthogonal projection can be applied as follows:

$$\sum_{j=1}^{M}\left(\sum_{k=1}^{N} X_{jk}\cdot X_{ik}\right)\alpha_j = \sum_{k=1}^{N} V_k X_{ik}$$

The terms $\alpha_j$ are terms containing the current for the jth coil. The control unit is configured to vary the value of the currents applied to each coil by varying the values of $\alpha_j$ in order to reduce the value of the magnetic field that would be measured by the magnetic field sensing elements collectively (e.g., as averaged amongst them) or individually to not exceed some desired pre-set threshold value corresponding to an appropriate level of field cancellation/nulling. To achieve cancelation the control unit 150 is configured to calculate the 'negative' values of currents with which each magnetic field generating coil must be driven by solving the following optimisation equation (note the negative sign appearing in the right-hand-side of this equation):

$$\sum_{j=1}^{M}\left(\sum_{k=1}^{N} X_{jk}\cdot X_{ik}\right)\alpha_j = -\sum_{k=1}^{N} V_k X_{ik}$$

Figure 20:
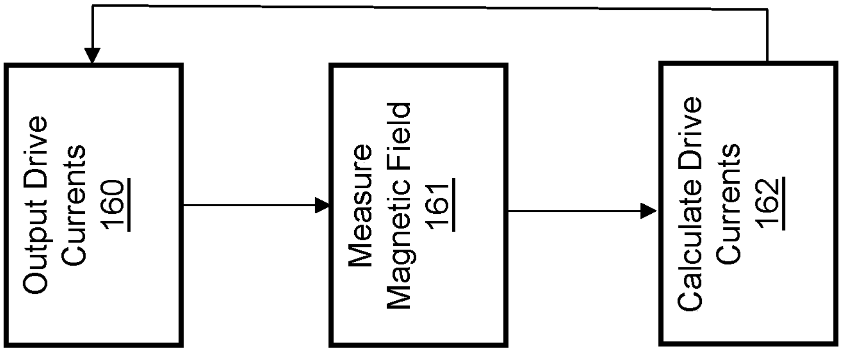
FIG. 20 shows schematically a process for controlling the elements of a magnetic field nulling apparatus.

In general, only a few iterations (typically, only one iteration) is necessary to get the best current solution for external magnetic field nulling/cancelling. The orthogonal basis for the orthogonal projection method is created in the calibration process. The orthogonal basis need only be created once and may subsequently be used by the control unit for all active cancellation/nulling using sensor data received from the magnetic field sensor array during active cancelling/nulling operations. This is very fast and simple process. Because of that any field distortions coming from differences between them, imprecisions, are removed. FIG. 20 summarises this process as comprising the steps of:

Step 160: Outputting, by the control unit 150, individual drive currents to magnetic field generating coils 102 in turn whilst no other coil receives a drive current.

Step 161: Measure, by the magnetic field sensor array 103, the magnetic field within the nulling region.

Step 162: Calculating, by the control unit 150, individual drive currents to apply to coils 102 by solving the optimisation equation and driving the coils with drive currents calculates accordingly.

FIGS. 19*a*, 19*b* and 19*c* show an example of two very different magnetic sources used as magnetic field generating elements in a regular spherical array 102 of 0.5 m diameter comprising 32 magnetic field generating elements in a Dual Geodesic Icosahedron array, surrounding an array of magnetic feed-back sensors 103. The magnetic field in the nulling region of the array shown in FIG. 19*b* corresponds to a case in which each magnetic field generating elements is configured to generate its local magnetic field via a circular current (e.g., a circular coil of 14 cm diameter). By contrast, the magnetic field in the nulling region of the array shown in FIG. 19*c* corresponds to a case in which each magnetic field generating elements is configured to generate its local magnetic field as a magnetic dipole field. In both cases nulling was obtained, across a nulling region of 8 cm diameter, in which an external ambient magnetic field exceeding 50 nT was reduced to about 0.5 nT average field and 0.027 nT/cm average field gradient (FIG. 19*b*) or about 1.0 nT average field and 0.044 nT/cm average field gradient (FIG. 19*c*). This reinforces that point that the magnetic field generating elements need not be coils and may be, for example, ant suitable magnetic field source that is configured to generate a dipole magnetic field instead.

Figure 22:
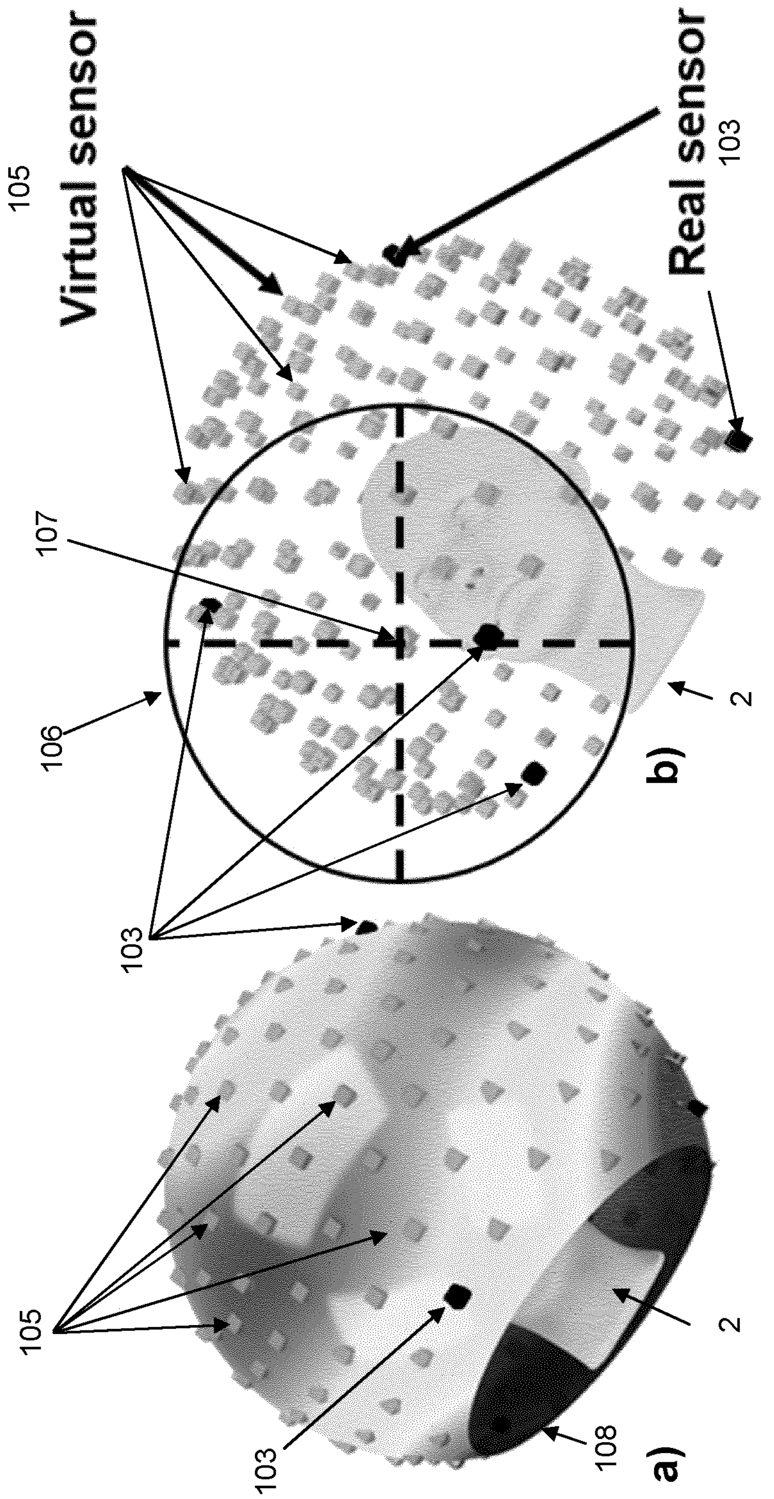
FIGS. 22*a* to 22*b* show schematic images of an array of virtual magnetic field sensing elements generated using a sub-array of real magnetic field sensing elements of a magnetic field nulling apparatus.

FIG. 22 shows an example of how the orthogonal projection method described above may use a number of magnetic field sensing elements (feedback sensors) 103 that are fewer in number than the number of magnetic field generating coils 102. In particular, if the number of sensors 103 is reduced to below about 40% of the number of magnetic field generating coils 102, then the performance of the above method may begin to deteriorate. To overcome this problem, the control unit 150 may be configured to generate magnetic field calibration values associated with notional "virtual" magnetic field sensors 105 located at any point within the nulling region by interpolating the calibration magnetic field values actually received by physical sensors 103 of the array of sensors. The control unit 150 may be configured to define a notional interpolation sphere 106 (see FIG. 22*b*) defined by a radius from a target position (coordinates: x, y, z) within the nulling region at which a virtual sensor calibration magnetic field value is to be interpolated. The control unit 150 may determine which of the real magnetic field sensors 103 are located within the notional sphere and may increase the radius of the sphere until at least two real sensors are within the sphere. Once the plurality of real sensors within the interpolation sphere are identified by the control unit, it then calculates a virtual value of the calibration magnetic field at the target location (x, y, z) by three-dimensional interpolation of the real calibration magnetic field values received by it from the plurality of real sensors within the interpolation sphere. This is then used in the process described above with reference to FIG. 20. Any number of separate target positions (coordinates: x, y, z) may be selected, such as positions corresponding to an array upon a notional spherical surface 108 (see FIG. 22*a*), with which to generate any number of virtual (i.e., interpolated) calibration magnetic field values. Interpolation may be as simple as summing the calibration magnetic field values (i.e., summing the appropriate x, y, z components of the respective fields) provided by the real sensors within an interpolation sphere and dividing the result (per field component) by the number of such real sensors within the interpolation sphere. When the difference between the number of coils 102 and feedback sensors 103 is significant, the orthogonal projection method may be improved in this way, by introducing virtual feedback sensors created by using readings from the real feedback sensors. The heat map 108 over the notional sphere upon which the feedback sensors (virtual and real) are located presents a map grey scale representing magnetic field flux density magnitude.

Figure 23A:
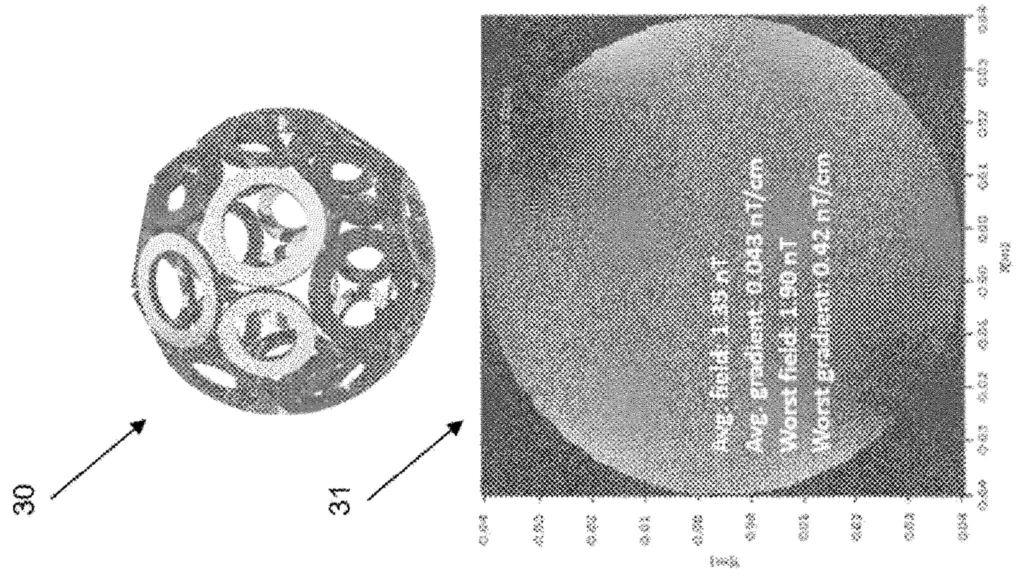
FIG. 23*a* and FIG. 23*b* and FIG. 23*c* show views of a magnetic field nulling apparatus with different respective numbers of magnetic field generating elements, together with a cross-sectional view of the magnetic field within the nulling regions thereof, respectively.
Figure 23B:
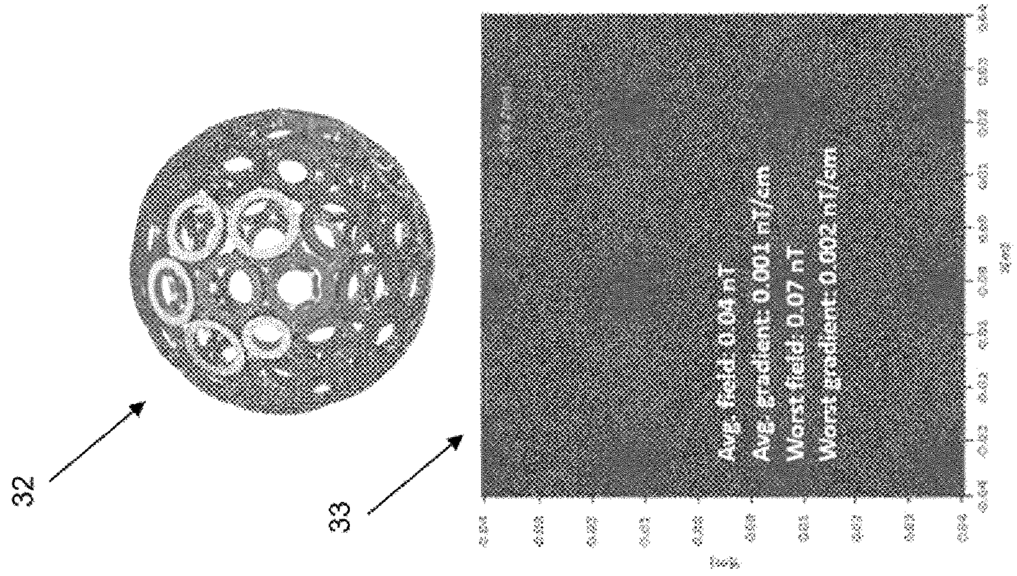
Figure 23C:
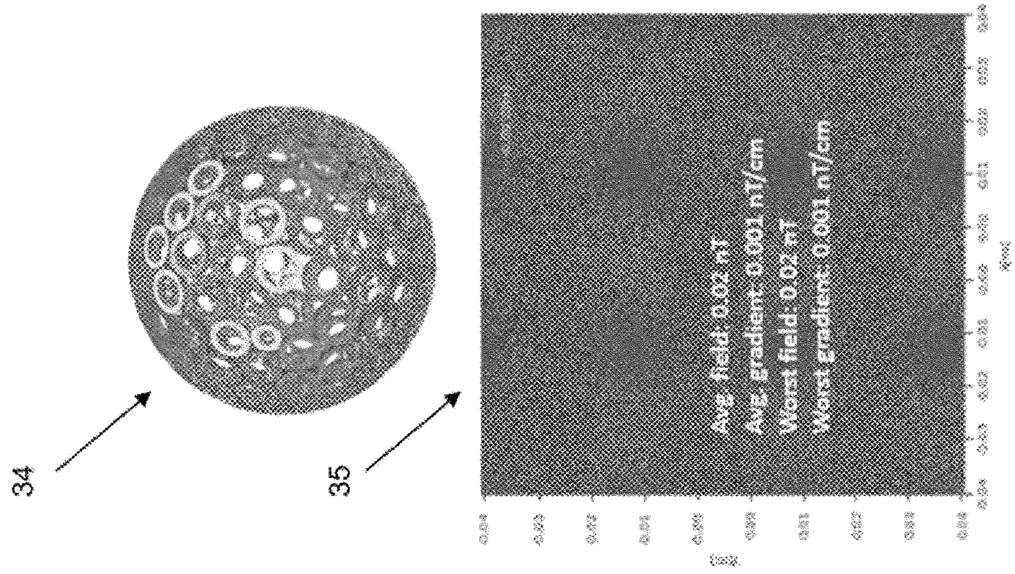

FIGS. 23*a*, 23*b* and 23*c* show examples of implementation of this method in which FIG. 23*a* shows an apparatus 30 having a coil array comprising 32 coils and 16 real sensors. The magnetic field nulling result 31 is shown for a 4 cm spherical nulling region. An average field of 1.35 nT with average gradient 0.043 nT/cm is achieved. FIG. 23*b* shows an apparatus 32 having a coil array comprising 92 coils and 16 real sensors and 76 virtual sensors. The magnetic field nulling result 33 is shown for a 4 cm spherical nulling region. An average field of 0.04 nT with average gradient 0.001 nT/cm is achieved. FIG. 23*c* shows an apparatus 34 having a coil array comprising 212 coils and 16 real sensors and 196 virtual sensors. The magnetic field nulling result 35 is shown for a 4 cm spherical nulling region. An average field of 0.02 nT with average gradient 0.001 nT/cm is achieved.

Figure 24:
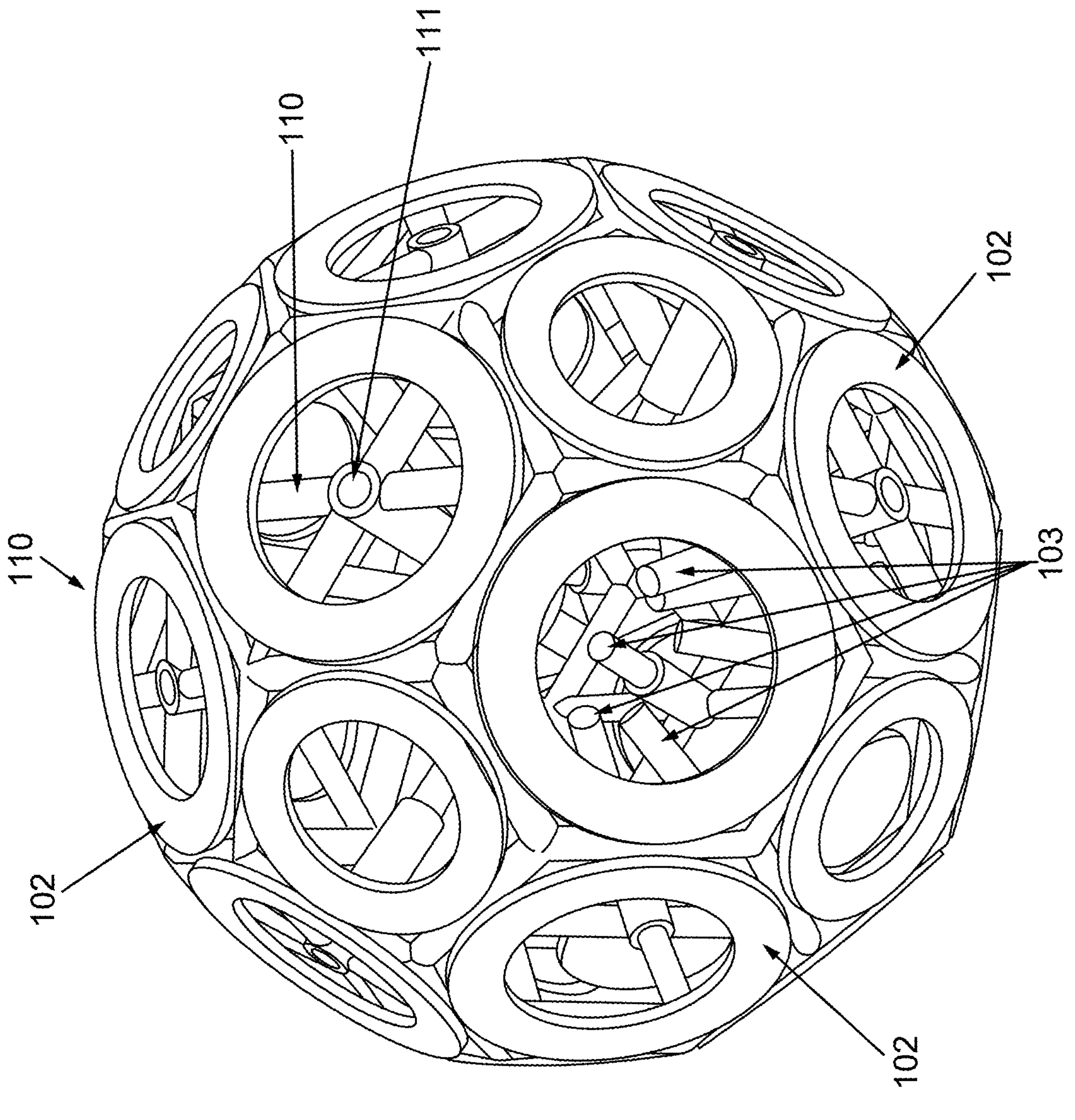
FIG. 24 shows a magnetic field nulling apparatus.

FIG. 24 shows a support scaffold 110 for supporting an array of magnetic field generating coils 102 and an array of magnetic field sensing elements 103. Sensor mounting with possibility to regulate distance to the array centre by pushing with a bolt. The support scaffold comprises a non-magnetic polyhedral frame. This is just one example of how coils and feedback sensors can be mounted. The lattice type is dual geodesic icosahedron with 32 faces. Each of the feedback sensors 103 is mounted on a respective one of a plurality of adjustable mounting rods 111 comprising a fixed end located at the centre of a local facet of the lattice and a free end within the volume enclosed by the lattice upon which a feedback sensor is mounted. Each mounting rod points radially inwardly into the volume surrounded by the array. The proximity of a given sensor to the centre of the coil lattice centre is adjustable by adjusting the length of the mounting rod to achieve adjustment for the optimum performance. For example, in this example each mounting rod is comprises a cylindrical tube containing a cylindrically shaped sensor which can moves forward and backward along the axis of the mounting rod to extend or retract the length of the mounting rod in a telescopic manner. The lattice support scaffold or frame holds coils and sensors in place in this way. Each of the coils can be fixed in different ways, such as by glue, or a lock system, of a gripper etc.

Figure 25:
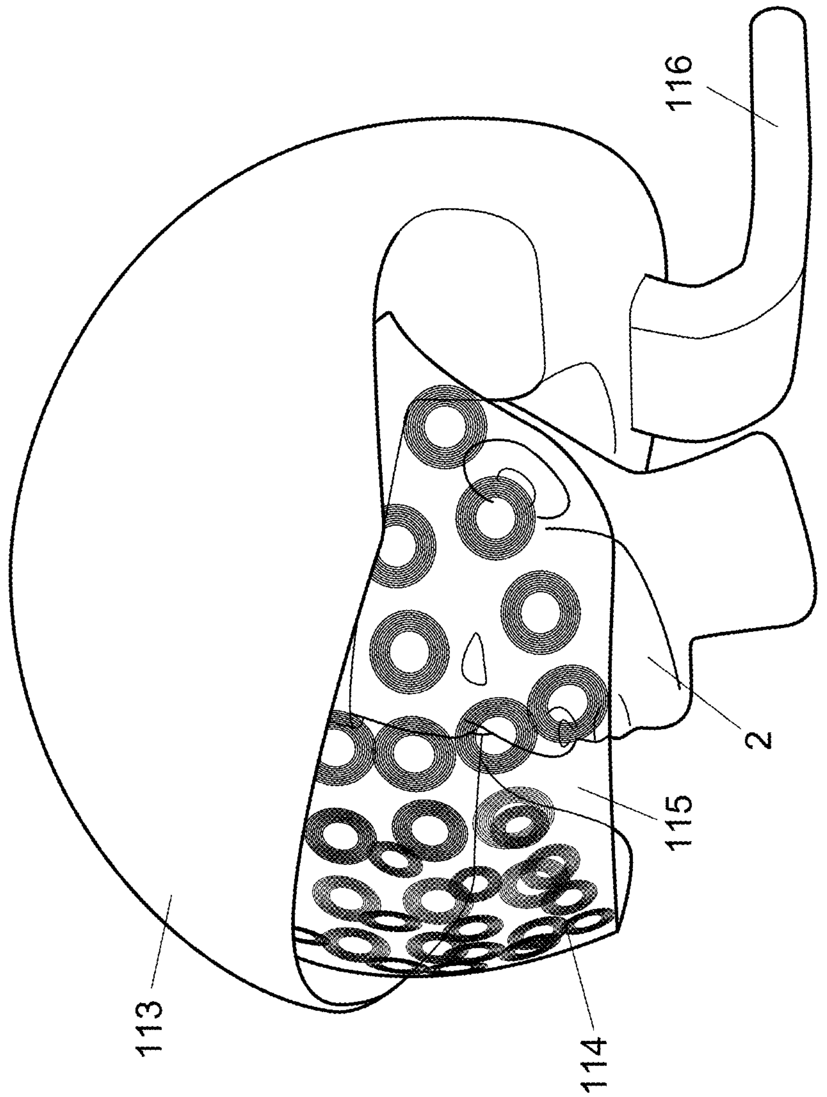
FIG. 25 shows a magnetic field nulling apparatus.

FIG. 25 shows another example of an apparatus according to the invention when used in a device for magnetoencephalography shielding, where an OPM based cap is used. A patient's head 2 is located within a hemispherical array of flat coils 114 mounted upon a transparent hemispherical support surface 115 formed from a non-magnetic material. For example, each coil wire may be deposited, printed, or formed by metal foil etching etc. A passive magnetic shield 113, for example mu-metal and aluminium layers, covers the magnetic field generating coil array. A support arm and housing 116 for electrical cables is provided.

The invention may permit reduced sensor costs for cancelling/nulling weak magnetic fields to achieve a nulled region in the μT-nT range or the nT-fT range.

Figure 26:
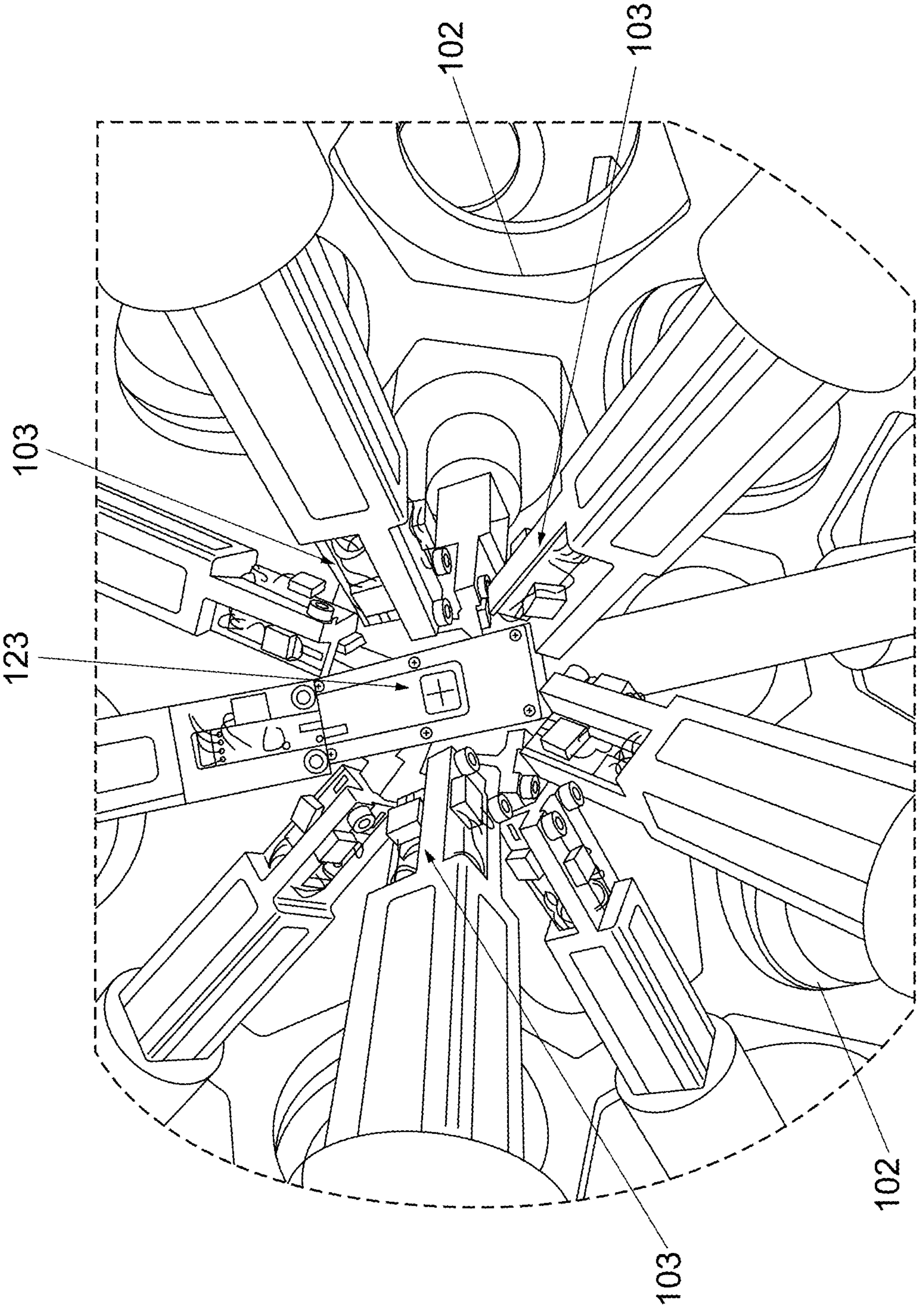
FIG. 26 shows a close-up view of a part of the magnetic field nulling apparatus of FIG. 24.

FIG. 26 shows an example of a magnetic field nulling apparatus that was constructed using a support scaffold in accordance with the design described above with reference to FIG. 24. The apparatus supported an array of magnetic field generating coils 102 and an array of magnetic field sensing elements 103. In this apparatus, thirty-two magnetic field generating coils 102 were employed and sixteen magnetic field sensing elements 103 are employed. The magnetic field generating coils were distributed over a geodesic icosahedron with a diameter of 0.5 m. The magnetic field sensing elements were disposed at positions suitably adjusted to obtain a spherical nulling volume with a diameter of 8 cm throughout which the magnetic field nulling apparatus is arranged to provide a null magnetic field. The magnetic field nulling apparatus was set in an ordinary building environment which was exposed to the geomagnetic field of approximately 50 μT. In addition, the magnetic field nulling apparatus was surrounded by magnetic objects in close proximity, including noise of electrical mains power supply sockets and cables. These magnetic objects, in combination with the geomagnetic field, created a magnetic field within the spherical nulling volume which was effectively nulled by operation of the magnetic field nulling apparatus.

FIG. 26 shows a close-up view of the magnetic field nulling apparatus which shows the array of magnetic field sensing elements 103 inside of the nulling apparatus. Each one of the magnetic sensing elements 103 comprises three magnetoimpedance sensors: each one arranged for measuring a magnetic field component in a respective one if three orthogonal axis directions, such as Sx, Sy and Sz in the x, y and z axis directions. An example of a suitable magnetoimpedance sensor is the nanotesla sensor manufactured by the Aichi Steel Corporation, Japan, and available under the model number "MI-CB-1DH". These sensors were modified to work in DC mode (as opposed to AC mode) according to instructions provided by Aichi Steel Corporation which are readily available to the skilled person. The magnetoimpedance sensors operated in DC operation mode and were calibrated in a low magnetic field environment. In the centre of the array of magnetic field sensing elements was located a fluxgate, magnetic sensing element 123 (produced by Bartington Instruments Limited, USA, under the product name "MAG-13") was placed as an additional reference sensor.

Due to the narrow dynamic range of the magnetoimpedance sensors used in this example, an initial geomagnetic cancelling was provided by collectively orienting the array of magnetic field generating coils 102 and the array of magnetic field sensing elements 103 of the nulling device appropriately. This was achieved by orienting the support scaffold (and the array of magnetic field generating coils 102 and magnetic field sensing elements 103 upon it) in a direction against the geomagnetic field vector and providing the coils of the array of magnetic field generating coils 102 with currents as described above with reference to the configuration presented in FIG. 11*a*. This set the internal magnetic field within the spherical nulling volume to be withing dynamic range of magnetoimpedance sensors.

The magnetic field nulling apparatus then underwent a calibration process as described above with reference to FIG. 18 and FIG. 19 so as to obtain an orthogonal basis matrix, as discussed above. Then, a scalar product was calculated and from this inverse matrix that is stored to be used in the active cancelation process.

The control unit (item 150, FIG. 19) calculated the 'negative' values of currents, $\alpha_j$, with which each magnetic field generating coil must be driven by solving the following 'orthogonal projection' optimisation equation (note the negative sign appearing in the right-hand-side of this equation):

$$\sum_{j=1}^{M}\left(\sum_{k=1}^{N} X_{jk}\cdot X_{ik}\right)\alpha_j = -\sum_{k=1}^{N} V_k X_{ik}$$

To calculate the 'negative' values of the coil currents in each active cancelling loop, readings from the magnetic sensing elements were placed into a measurement matrix: $[V_1, V_2, V_3, \ldots, V_N]$. The measurements of a magnetic field include measurements (Sx, Sy, Sz) of three orthogonal field components by each of the sensors and these are represented in the elements of the measurement matrix by:

$$Sx_1, Sy_1, Sz_1, Sx_2, Sy_2, Sz_2 \ldots = V_1, V_2, V_3, V_4, V_5, V_6 \ldots$$

The dot product of the matrix and the orthogonal basis was calculated as:

$$\sum_{k=1}^{N} V_k X_{ik}$$

Here, the elements $X_{ik}$ correspond to coil magnetic field components (Bx, By, Bz) that it is known (i.e., based on knowledge of the response of each coil to a given drive current) would be generated by individual coils in three orthogonal directions in response to being driven by drive current represented by currents, α, and these are represented in the above optimisation equation via:

$$Bx_{11}, By_{11}, Bz_{11}, Bx_{12}, By_{12}, Bz_{12} \ldots = X_{11}, X_{12}, X_{13}, X_{14}, X_{15}, X_{16} \ldots$$

Using the resulting dot product, the control unit calculated is configured to invert the above 'orthogonal projection' optimisation equation. The result consists of matrix containing individual values, $\alpha_j$, for the currents with which to drive the coils 102 individually.

In the present example, a 2.8 GHZ Quad Core Controller obtained from National Instruments Corporation under the product code "PXIe-8861", was used. This was equipped with two PXI-6349 simultaneous analogue to digital converters (ADC) to read magnetic sensing elements. These were obtained from National Instruments Corporation under the product code "PXI-6349". Digital to analogue converters (DAC), also obtained from National Instruments Corporation under the product code "PXIe-6739" were arranged to provide current sources via which to provide drive currents for the magnetic field generating coils. The process of measuring magnetic fields, (Sx, Sy, Sz) etc., finding 'negative' currents, $\alpha_j$, and applying those currents to the coils, was found to take less than 250 µs. This process is amenable to being made quicker by employing a field-programmable gate array (FPGA).

Figure 27A:
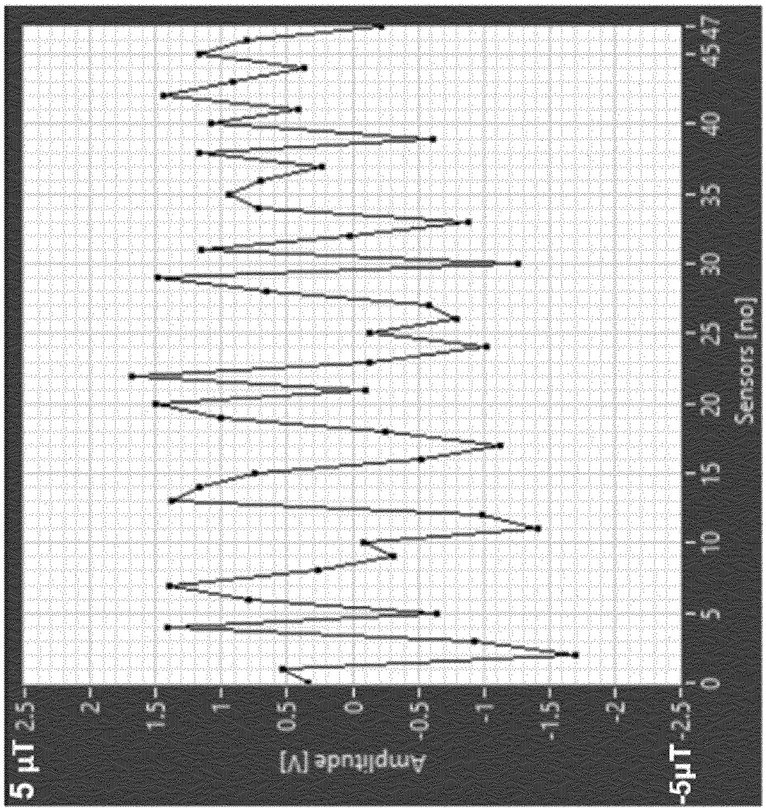
FIGS. 27*a*, 27*b* and 27*c* shows a graphically some examples of sensor signals generated by sensors of the magnetic field nulling apparatus of FIG. 26.

FIG. 27*a* shows readings (Sx, Sy, Sz) taken from sixteen magnetic sensing elements 103. This corresponds to forty-eight (i.e., 16×3=48) single magnetoimpedance magnetic sensors, being disturbed by a non-uniform magnetic field.

Figure 27B:
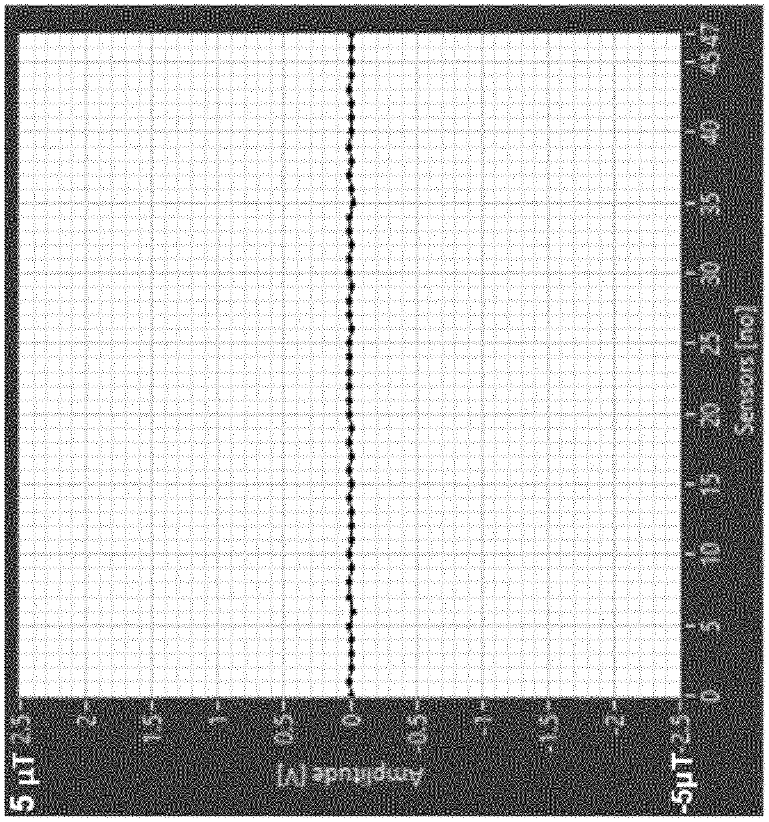
Figure 27C:
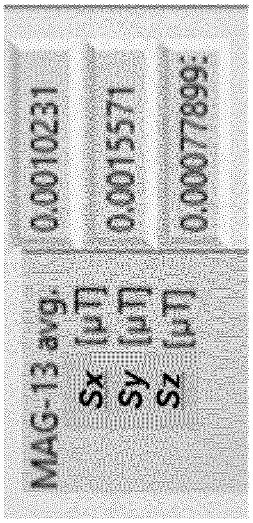

FIG. 27*b* shows same reading after running a single calculation of the orthogonal projection (nulling) algorithm. Reference magnetic sensors readings (Sx, Sy, Sz) from the fluxgate, magnetic sensing element 123 ("MAG-13") are presented on FIG. 27*c*. The vertical scale of these figures is measured in volts (V) whereby a reading of 2.5V corresponds to a measurement of 5 µT.

When active cancelling is running in the magnetic field nulling apparatus, the support scaffold can be rotated to any position against geomagnetism and it was found that it could be approached with magnetic objects or AC magnetic sources without deterioration to the nulling of the magnetic field environment in the nulling zone. Furthermore, it was found that any errors due to electronic components of the device changing their properties, physical dimension intolerances, had an effect equivalent to a variation of the external magnetic field and the device was found to respond by providing a cancelling of the effects that these errors would otherwise have produced on the nulling of the magnetic field environment.

The features disclosed in the foregoing description, or in the following claims, or in the accompanying drawings, expressed in their specific forms or in terms of a means for performing the disclosed function, or a method or process for obtaining the disclosed results, as appropriate, may, separately, or in any combination of such features, be utilised for realising the invention in diverse forms thereof.

While the invention has been described in conjunction with the exemplary embodiments described above, many equivalent modifications and variations will be apparent to those skilled in the art when given this disclosure. Accordingly, the exemplary embodiments of the invention set forth above are considered to be illustrative and not limiting. Various changes to the described embodiments may be made without departing from the spirit and scope of the invention.

For the avoidance of any doubt, any theoretical explanations provided herein are provided for the purposes of improving the understanding of a reader. The inventors do not wish to be bound by any of these theoretical explanations.

Any section headings used herein are for organizational purposes only and are not to be construed as limiting the subject matter described.

Throughout this specification, including the claims which follow, unless the context requires otherwise, the word "comprise" and "include", and variations such as "comprises", "comprising", and "including" will be understood to imply the inclusion of a stated integer or step or group of integers or steps but not the exclusion of any other integer or step or group of integers or steps.

It must be noted that, as used in the specification and the appended claims, the singular forms "a," "an," and "the" include plural referents unless the context clearly dictates otherwise. Ranges may be expressed herein as from "about" one particular value, and/or to "about" another particular value. When such a range is expressed, another embodiment includes from the one particular value and/or to the other particular value. Similarly, when values are expressed as approximations, by the use of the antecedent "about," it will be understood that the particular value forms another embodiment. The term "about" in relation to a numerical value is optional and means for example +/−10%.

References herein to "diameter" refer to a straight line passing from side to side through the centre of a structure, array, body or figure, especially (but not exclusively) a circle or sphere.

The invention claimed is:

1. An apparatus for nulling a magnetic field within a nulling region in an ambient magnetic field comprising:

a plurality of separate magnetic field generating elements placed at separate respective locations surrounding the nulling region for generating respective nulling magnetic fields extending into the nulling region, wherein the plurality of magnetic field generating elements are arranged in a first array;

a plurality of magnetic field sensing elements placed at a plurality of separate respective locations within the nulling region for sensing respective values of the magnetic field within the nulling region wherein the plurality of magnetic field sensing elements are arranged in a second array and the size of a diameter of the second array of magnetic field sensing elements is at least 30% of the size of a diameter of the first array of magnetic field generating elements; and a feedback control unit for controlling the values of the respective nulling magnetic fields generated by each of the plurality of magnetic field generating elements in response to values of the magnetic field sensed by the plurality of magnetic field sensing elements by driving the magnetic field generating elements with respective electric currents that reduce the magnetic field values detected by respective magnetic field sensing elements to values not exceeding a pre-set threshold value corresponding to a pre-set nulling of the magnetic field within the nulling region.

2. The apparatus according to claim 1 wherein the magnetic field generating elements comprise electrically conductive coils adapted for conducting said electric currents.

3. The apparatus according to claim 1 wherein the first array of the plurality of magnetic field generating elements has a shape according to a three-dimensional reference surface and surrounds the nulling region.

4. The apparatus according to claim 1 wherein the second array of the plurality of magnetic field sensing elements has a shape according to a three-dimensional reference surface.

5. The apparatus according to claim 1, wherein the second array is substantially concentric with the first array.

6. The apparatus according to claim 1 wherein said separate respective locations of the plurality of separate magnetic field generating elements in the first array are defined according to a regular lattice.

7. The apparatus according to claim 1 wherein said separate respective locations of the plurality of magnetic field sensing elements in the second array are defined according to a regular lattice.

8. The apparatus according to claim 1 wherein the plurality of magnetic field generating elements are arranged at said separate respective locations substantially equidistant from the centre of the nulling region thereby defining a substantially spherical array surrounding the nulling region as the first array.

9. The apparatus according to claim 1 wherein the plurality of magnetic field sensing elements are arranged at said separate respective locations substantially equidistant from the centre of the nulling region thereby defining a substantially spherical array within the nulling region as the second array.

10. The apparatus according to claim 1 wherein the size of a diameter of the second array of magnetic field sensing elements is in the range of about 30% to about 90% of the size of a diameter of the first array of magnetic field generating elements.

11. The apparatus according to claim 1 wherein the plurality of magnetic field generating elements comprises at least 10 separate magnetic field generating elements.

12. The apparatus according to claim 1 wherein the plurality of magnetic field generating elements comprises at least 50 separate magnetic field generating elements.

13. The apparatus according to claim 1 wherein the plurality of magnetic field generating elements comprises at least 200 separate magnetic field generating elements.

14. The apparatus according to claim 1 wherein the feedback control unit comprises input terminals connected to the output of the magnetic field sensing elements and comprises output terminals connected to the input terminals of associated magnetic field generating elements.

15. The apparatus according to claim 1 wherein the threshold value is not greater than $5\times10^{-9}$ Tesla.

16. The apparatus according to claim 1 wherein the threshold value is not greater than $5\times10^{-10}$ Tesla.

17. A method for nulling a magnetic field within a nulling region in an ambient magnetic field comprising:

providing a plurality of separate magnetic field generating elements placed at separate respective locations surrounding the nulling region for generating respective nulling magnetic fields extending into the nulling region, wherein the plurality of magnetic field generating elements are arranged in a first array;

providing a plurality of magnetic field sensing elements placed at a plurality of separate respective locations within the nulling region for sensing respective values of the magnetic field within the nulling region wherein the plurality of magnetic field sensing elements are arranged in a second array and the size of a diameter of the second array of magnetic field sensing elements is at least 30% of the size of a diameter of the first array of magnetic field generating elements; and controlling the values of the respective nulling magnetic fields generated by each of the plurality of magnetic field generating elements in response to values of the magnetic field sensed by the plurality of magnetic field sensing elements by driving the magnetic field generating elements with respective electric currents that reduce the magnetic field values detected by respective magnetic field sensing elements to values not exceeding a pre-set threshold value corresponding to a pre-set nulling of the magnetic field within the nulling region.

18. The method according to claim 17 wherein the magnetic field generating elements comprise electrically conductive coils and the method includes conducting said respective electric currents through respective ones of said coils.

19. The method according to claim 17 wherein the first array of the plurality of magnetic field generating elements has a shape according to a three-dimensional reference surface and surrounds the nulling region.

20. The method according to claim 17 wherein the second array of the plurality of magnetic field sensing elements has a shape according to a three-dimensional reference surface.

21. The method according to claim 17 wherein the second array is substantially concentric with the first array.

22. The method according to claim 17 wherein said separate respective locations of the plurality of separate magnetic field generating elements in the first array are defined according to a regular lattice.

23. The method according to claim 17 wherein said separate respective locations of the plurality of separate magnetic field sensing elements in the second array are defined according to a regular lattice.

24. The method according to claim 17 including providing the plurality of magnetic field generating elements as arranged at said separate respective locations substantially equidistant from the centre of the nulling region thereby defining a substantially spherical array surrounding the nulling region as the first array.

25. The method according to claim 17 including providing the plurality of magnetic field sensing elements as arranged at said separate respective locations substantially equidistant from the centre of the nulling region thereby defining a substantially spherical array within the nulling region as the second array.

26. The method according to 17 wherein the size of a diameter of the second array of magnetic field sensing elements is in the range of about 30% to about 90% of the size of a diameter of the first array of magnetic field generating elements.

27. The method according to claim 17 including providing the plurality of magnetic field generating elements to comprise at least 10 separate magnetic field generating elements.

28. The method according to claim 17 including providing the plurality of magnetic field generating elements to comprise at least 50 separate magnetic field generating elements.

29. The method according to claim 17 including providing the plurality of magnetic field generating elements to comprise at least 200 separate magnetic field generating elements.

30. The method according to claim 17 including receiving inputs at a feedback control unit that correspond to outputs from the magnetic field sensing elements and providing outputs from the feedback control unit comprising control signals that are input to associated magnetic field generating elements.

31. The method according to claim 17 wherein the threshold value is not greater than $5\times10^{-9}$ Tesla.

32. The method according to claim 17 wherein the threshold value is not greater than $5\times10^{-10}$ Tesla.

33. The apparatus according to claim 1 wherein the feedback control unit is arranged to determine a set of a plurality of optimal respective electric currents with which to drive the corresponding plurality of magnetic field generating elements by applying an orthogonal projection algorithm.

34. The apparatus according to claim 1 wherein said separate respective locations of the plurality of separate magnetic field generating elements in the first array are defined according to a geodesic lattice.

35. The apparatus according to claim 1 wherein the size of a diameter of the second array of magnetic field sensing elements is between about 40% and about 90% of the size of a diameter of the first array of magnetic field generating elements.

36. The apparatus according to claim 1 wherein the feedback control unit is configured to control said values of the respective nulling magnetic fields generated by each of the plurality of magnetic field generating elements in response to values of the magnetic field sensed by the plurality of magnetic field sensing elements by driving the magnetic field generating elements with respective electric currents that reduce the magnetic field values detected by respective magnetic field sensing elements to values corresponding to an average magnetic field gradient not exceeding about 10 nT/cm within the nulling region.

37. The method apparatus according to claim 17 comprising determining a set of a plurality of optimal respective electric currents with which to drive the corresponding plurality of magnetic field generating elements by applying an orthogonal projection algorithm.

38. The method according to claim 17 wherein said separate respective locations of the plurality of separate magnetic field generating elements in the first array are defined according to a geodesic lattice.

39. The method according to claim 17 wherein the size of a diameter of the second array of magnetic field sensing elements is between about 40% and about 90% of the size of a diameter of the first array of magnetic field generating elements.

40. The method according to claim 17 comprising controlling said values of the respective nulling magnetic fields generated by each of the plurality of magnetic field generating elements in response to values of the magnetic field sensed by the plurality of magnetic field sensing elements by driving the magnetic field generating elements with respective electric currents that reduce the magnetic field values detected by respective magnetic field sensing elements to values corresponding to an average magnetic field gradient not exceeding about 10 nT/cm within the nulling region.

* * * * *